(12) United States Patent
Tay et al.

(10) Patent No.: US 11,679,064 B2
(45) Date of Patent: Jun. 20, 2023

(54) SYNTHESIS OF ANTIMICROBIAL SILSESQUIOXANE-SILICA HYBRIDS

(71) Applicant: KIMMERLING HOLDINGS GROUP, LLC, Marietta, GA (US)

(72) Inventors: Franklin R. Tay, Augusta, GA (US); Shi-qiang Gong, Wuhan (CN); Kirk Kimmerling, Marietta, GA (US)

(73) Assignee: KIMMERLING HOLDINGS GROUP, LLC, Marietta, GA (US)

( * ) Notice: Subject to any disclaimer, the term of this patent is extended or adjusted under 35 U.S.C. 154(b) by 101 days.

(21) Appl. No.: 17/240,409

(22) Filed: Apr. 26, 2021

(65) Prior Publication Data

US 2022/0041811 A1  Feb. 10, 2022

Related U.S. Application Data

(63) Continuation of application No. 16/241,078, filed on Jan. 7, 2019, now Pat. No. 10,995,181, which is a continuation of application No. 14/907,799, filed as application No. PCT/US2014/051243 on Aug. 15, 2014, now Pat. No. 10,189,954.

(60) Provisional application No. 61/959,177, filed on Aug. 16, 2013.

(51) Int. Cl.
| | |
|---|---|
| *A61K 6/20* | (2020.01) |
| *C08G 77/442* | (2006.01) |
| *C01B 33/18* | (2006.01) |
| *C08K 3/36* | (2006.01) |
| *C07F 7/18* | (2006.01) |
| *C07F 7/21* | (2006.01) |
| *C01B 33/113* | (2006.01) |
| *C08G 83/00* | (2006.01) |
| *C07F 7/08* | (2006.01) |
| *C08F 230/08* | (2006.01) |
| *C08G 77/20* | (2006.01) |
| *A01N 55/00* | (2006.01) |
| *C08G 77/26* | (2006.01) |
| *C08F 236/00* | (2006.01) |

(52) U.S. Cl.
CPC .............. *A61K 6/20* (2020.01); *A01N 55/00* (2013.01); *C01B 33/113* (2013.01); *C01B 33/18* (2013.01); *C07F 7/0838* (2013.01); *C07F 7/188* (2013.01); *C07F 7/21* (2013.01); *C08F 230/08* (2013.01); *C08G 77/20* (2013.01); *C08G 77/26* (2013.01); *C08G 77/442* (2013.01); *C08G 83/001* (2013.01); *C08K 3/36* (2013.01); *C08F 236/00* (2013.01)

(58) Field of Classification Search
CPC ........ C08G 77/26; C09C 1/3081; C09C 1/309
USPC ....................................................... 528/38
See application file for complete search history.

(56) References Cited

U.S. PATENT DOCUMENTS

| 10,181,954 B2 * | 1/2019 | Naik ..................... H04L 9/3247 |
| 10,995,181 B2 * | 5/2021 | Tay ..................... C08F 230/085 |
| 2013/0230676 A1 * | 9/2013 | Blizzard ................ C08G 77/58 |
| | | 521/154 |

FOREIGN PATENT DOCUMENTS

| JP | 2007169507 | 7/2007 |
| WO | WO 2010/044875 | * 4/2010 |

OTHER PUBLICATIONS

"Quaternary Ammonium Sllane-functionalized, Methacrylate Resin Composition with Antimicrobial Activities and Self-repair Potential" authored by Gong et al. and published in Acta Biomaterialia (2012) 8, 3270-3282.*

Ahlstrom, et al., "The effect of hydrocarbon chain length, pH, and temperature on the binding and bactericidal effect of amphiphilic betaine esters on SdmneZb typhimurium", APMIS 107: 318-24, 1999.

Bag, et al., "Synthesis of UV-curable difunctional silane monomer based on 3-methacryloxy propyl trimethoxy silane (3-MPTS) and its UV-curing characteristics and thermal stability", J. Appl. Poly. Sci. 2010, 115, 2352 (Abstract).

Bonhomme, et al., "Advanced Solid-State NMR Techniques for the Characterization of Sol-Gel-Derived Materials", Acc. Chem. Res. 2007, 40, 738-746.

Buchel, et al., "A Novel Pathway for Synthesis of Submicrometer-Size Solid Core/Mesoporous Shell Silica Spheres", Adv. Mater. 1998, 10, No. 13 (3 pages).

Chen, et al., "Co-delivery of Doxorubicin and Bcl-2 siRNA by Mesoporous Silica Nanoparticles Enhances the Efficacy of Chemotherapy in Multidrug Resistant Cancer Cells", Small 2009, pp. 2673-2677.

Chen, et al., "Sol-Gel Synthesis and Micro structure Analysis of Amino-Modified Hybrid Silica Nanoparticles from Aminopropyltriethoxy silane and Tetraethoxy silane", J. Am. Ceram. Soc., 92 [9] 2074-2082 (2009).

Choi, et al., "Amphiphilic organosilane-directed synthesis of crystalline zeolite with tunable mesoporositv", Nature Materials, vol. 5, Sep. 2006 (6 pages).

Deng, et al., "Novel NafiodORMOSIL Hybrids via in Situ Sol-Gel Reactions, 1. Probe of ORMOSIL Phase Nanostructures by Infrared Spectroscopy", Chem. Mater. 1995, 7, 2259-2268.

Fredrick, et al., "Factors governing partial coalescence in oil-in-water emulsions", Adv. Colloid Interface Sci. 2010, 153, 30 (Abstract).

Fujimoto, et al., "Surfactant-free synthesis of lamellar and wormhole-like silica mesostructures by using 1-alkynyltrimethoxysilanes", J. Mater. Chem., 2006, 16, 986 (9 pages).

(Continued)

Primary Examiner — Marc S Zimmer
(74) Attorney, Agent, or Firm — Meunier Carlin & Curfman LLC

(57) ABSTRACT

One-pot synthetic methods are disclosed for synthesizing curable, antimicrobial silsesquioxane-silica hybrids by hydrolytically co-condensing a tetraalkoxysilane with two different trialkoxysilanes. Particles are also disclosed that are substantially spherical and have an ordered lamellar internal structure. In addition, polymers prepared front the curable, antimicrobial silsesquioxane-silica hybrids and co-monomers are disclosed.

16 Claims, 15 Drawing Sheets

(56) References Cited

OTHER PUBLICATIONS

Gong, Shi-qiang, et al. "An ORMOSIL-containing orthodontic acrylic resin with concomitant improvements in antimicrobial and fracture toughness properties." PloS one 7.8 (2012): e42355.

Gong, et al., "Effect of water-aging on the antimicrobial activities of an ORMOSIL-containing orthodontic acrylic resin", Acta Biomaterialia 9 (2013) pp. 6964-6973.

Gong, et al., "Quaternary ammonium silane-functionalized, methacrylate resin composition with antimicrobial activities and self-repair potential", Acta Biomaterialia 8 (2012) pp. 3270-3282.

Gong, et al., "Synthesis of antimicrobial silsesquioxane-silica hybrids by hydrolytic co-condensation of alkoxvsilanes", Polvm. Chem., 2014, 5, 454 (9 pages).

Hoffman, et al., "Silica-Based Mesoporous Organic-Inorganic Hybrid Materials", Angew. Chem. Int. Ed. 2006, 45, 3216-3251.

Huo, et al., "Surfactant Control of Phases in the Synthesis of Mesoporous Silica-Based Materials", Chem. Mater. 1996, 8, 1147-1160.

Koytepe, et al., "Synthesis and Dielectric Properties of Polyimide-Titania Hybrid Composites", J. Inorg. Organomet. Polym. (2008) vol. 18, pp. 222-228.

Mackenzie, et al., "Rubbery ormosils and their applications", J. Non-Cryst. Solids, 1992, vols. 147-148, pp. 271-279.

Medda, et al., "Inorganic-organic hybrid coatings on polycarbonate Spectroscopic studies on the simultaneous polymerizations of methacrylate and silica networks", Journal of Non-Crystalline Solids 318 (2003) 149-156.

Mori, et al., "Synthesis and Characterization of Water-Soluble Silsesquioxane-Based Nanoparticles by Hydrolytic Condensation of Triethoxy silane Derived from 2-Hydroxyethyl Acrylate", Langmuir 2007, 23, 9014-9023.

Nicole, et al., "Integrative Approaches to Hybrid Multifunctional Materials: From Multidisciplinary Research to Applied Technologies", Adv. Mater. 2010, 22, 3208-3214.

Novak, "Hybrid Nanocomposite Materials—Between Inorganic Glasses and Organic Polymer", Adv. Mater. 1993, vol. 5, No. 6 (12 pages).

Oliver and Pharr, An improved technigue for determining hardness and elastic modulus using load and displacement sensing indentation.

Ruiz-Hitzky, et al., "Novel Organic±lnorganic Mesophases: Self-Templating Synthesis and Intratubular Swellina", Adv. Mater. 2002, 14, No. 6, Mar. 18 (5 pages).

Ruiz-Kitzky, et al., "Hybrid and biohybrid silicate based materials: molecular vs. block-assembling bottom-up processes", Chem. Soc. Rev., 2011, 40, 801-828.

Sanchez, et al., "Optical Properties of Functional Hybrid Organic-Inorganic Nanocomposites", Adv. Mater. 2003, vol. 15, No. 23 (26 pages).

Shimojima, et al., "Designed Synthesis of Nanostructured Siloxane-Organic Hybrids from Amphiphilic Silicon-Based Precursors", The Chemical Record, vol. 6, 53-63 (2006).

Shimojima, et al., "Inorganic-Organic Layered Materials Derived via the Hydrolysis and Polycondensation of Trialkoxy(alkyl)silanes", Bulletin of the Chemical Society of Japan, 1997, vol. 17, No. 11, pp. 2847-2853.

Shimojima, et al., "Structural Control of Multilayered Inorganic-Organic Hybrids Derived from Mixtures of Alkyltriethoxy silane and Tetraethoxy silane", Langmuir 2002, 18, 1144-1149.

Silva, et al., "Acid and Base Catalysts in the Hybrid Silica Sol-Gel Process", Journal of Colloid and Interface Science 195, 381-397 (1997).

Stober, et al., "Controlled Growth of Monodisperse Silica Spheres in the Micron Size Range", Journal of Colloid and Interface Science 26, 62-69 (1968).

Van Blaaderen, et al., "Synthesis and Characterization of Monodisperse Colloidal Organo-silica Spheres", Journal of Colloid and Interface Science, vol. 156, pp. 1-18 (1993).

Wu, et al., "Dynamics and corrosion resistance of amine-cured organically modified silicate coatings on aluminum alloys", Thin Solid Films, 2006, 513, pp. 84-89.

Xie, et al., "Thermal Degradation Chemistry of Alkyl Quaternary Ammonium Montmorillonite", Chem. Mater. 2001, 13, 2979 (12 pages).

Naka, et al., "One-pot synthesis of organo-functionalized monodisperse silica particles in W/O microemulsion and the effect of functional groups on addition into polystyrene", Colloids Surf. A. Physicochem. Eng. Aspects, 2010, vol. 361, pp. 162-168.

Zhang, et al., "One-step sol-gel preparation of PDMS-silica ORMOSILs as environment-resistant and crack-free thick antireflective coatinos" J. Mater. Chem., 2012, 22, 13132 (9 pages).

International Search Report and Written Opinion of the International Searching Authority dated Oct. 28, 2014 for international application PCT/US2014/051243, filed on Aug. 15, 2014 and published as WO 2015/023934 on Feb. 19, 2015 (Applicant—Kimmerling Holdings//Inventor—Tav, et al.) (9 pages).

\* cited by examiner

SYNTHESIS OF ANTIMICROBIAL SILSESQUIOXANE-SILICA HYBRIDS

CROSS-REFERENCE TO RELATED APPLICATIONS

This application is a continuation of U.S. application Ser. No. 16/241,078, filed Jan. 7, 2019 (now U.S. Pat. No. 10,995,181), which is a continuation of U.S. application Ser. No. 14/907,799, filed Jan. 26, 2016 (now U.S. Pat. No. 10,189,954), which is a U.S. National Phase Application of International Application No. PCT/US2014/051243, filed Aug. 15, 2014, which claims priority to U.S. Provisional Application No. 61/959,177, filed Aug. 16, 2013, each of which are hereby incorporated by reference in its entirety.

FIELD OF THE INVENTION

The present invention generally relates to methods of preparing silsesquioxane-silica hybrids. More particularly, it relates, inter alia, to one-pot synthetic methods are disclosed for synthesizing curable, antimicrobial silsesquioxane-silica hybrids and particles containing such hybrids.

BACKGROUND OF THE INVENTION

Organically-modified silicates are organic-inorganic hybrid materials in which the organic moieties are covalently linked to the siloxane backbone (L. Nicole, L. Rozes, C. Sanchez, *Adv. Mater.*, 2010, 22, 3208). Their rheological behavior may be modified by varying the precursor ratios, resulting in materials exhibiting rubbery or brittle characteristics (J. D. Mackenzie, Y. J. Chung, Y. Hu, *J. Non-Cryst. Solids*, 1992, 147-148, 271). Silsesquioxanes ($[RSiO_{1.5}]_n$) are specific examples of organically-modified silicates in which R is hydrogen or any organic group (e.g., alkyl, alkylene, aryl, etc.). Silsesquioxanes or silsesquioxane-silica hybrids are synthesized using a Stöber-like sol-gel route (W. Stöber, A. Fink, E. Bohn, *J. Colloid Interface Sci.*, 1968, 26, 62), via hydrolytic condensation of trialkoxysilanes, bridged alkoxides or co-condensation between a tetra-alkoxysilane and a trialkoxysilane (F. Hoffmann, M. Cornelius, J. Morell, M. Fröba, *Angew. Chem. Int. Ed.*, 2006, 45, 3216; H. Mori, Y. Miyamura, T. Endo, *Langmuir*, 2007, 23, 9014; E. Ruiz-Hitzky, P. Aranda, M. Darder, M. Ogawa, *Chem. Soc. Rev.*, 2011, 40, 801). By controlling the organic-inorganic composition, as well as functionality of these hybrid materials, a wide variety of silicate-based hybrid materials may be produced for applications in the fields of catalysis (F. Hoffmann, M. Cornelius, J. Morell, M. Fröba, *Angew. Chem. Int. Ed.*, 2006, 45, 3216), optical devices (C. Sanchez, B. Lebeau, F. Chaput, J. P. Boilot, *Adv. Mater.*, 2003, 15, 1969), coating and polymer science (X. X. Zhang, B. B. Xia, H. P. Ye, Y. L. Zhang, B. Zhao, L. H. Yan, H. B. Lv, B. Jiang, *J. Mater. Chem.*, 2012, 22, 13132; B. M. Novak, *Adv. Mater.*, 1993, 5, 422).

The introduction of reactive functionalities to silsesquioxanes may be achieved via post-synthetic surface functionalization procedures (grafting), which are based upon chemical reaction of silica particles with coupling agents bearing organic functional groups. However, the limitations of the grafting method are that there are relatively few silanol groups available on the surface of the silica particles and the procedure is time-consuming. In addition, this method generally results in particles containing only one type of functional group.

Recently, efforts have been made to explore the ability of organosilanes with surfactant chain-bearing groups to self-direct the hydrolysis and condensation of alkoxysilane precursors into structures with mesoporous characteristics (G. Büchel, K. Klaus, K. K. Unger, A. Matsumoto, K. Tsutsumi, *Adv. Mater.*, 1998, 10, 1036; E. Ruiz-Hitzky, S. Letaïef, V. Prévot, *Adv. Mater.*, 2002, 14, 439; Y. Fujimoto, A. Shimojima, K. Kuroda, *J. Mater. Chem.*, 2006, 16, 986; M. Choi, H. S. Cho, R. Sricastava, C. Venkatesan, D. H. Choi, R. Ryoo, *Nat. Mater.*, 2006, 5, 718). Although the mechanisms of using surfactant silanes to facilitate formation of particles with tailored mesostructures (i.e., mesoporous, lamellar, and worm-like mesostrucutures) were well understood, little is known regarding the synthesis of mesostructured hybrid materials with dual functionalities.

Accordingly, there is a need for methods of preparing silsesquioxane-silica hybrids and for preparing particles containing these hybrids having mesoporous characteristics. The methods and compositions of the present invention are directed toward these, as well as other, important ends.

SUMMARY OF THE INVENTION

Direct synthesis, in which silica-based hybrid particles are generated by co-condensation of tetra-alkoxysilane with terminal trialkoxysilane, represents a more advantageous route, with the organic functionality distributed within the synthesized materials instead of the surface of the materials (A. Van Blaaderen, A. Vrij, *J. Colloid Interface Sci.*, 1993, 156, 1; C. R. Silva, C. Airoldi, *J Colloid Interface Sci.*, 1997, 195, 381; S. Chen, S. Hayakawa, Y. Shirosaka, E. Fujii, K. Kawabata, K. Tsuru, A. Osaka, J. Am. Ceram. Soc., 2009, 92, 2074; Y. Naka, Y. Komori, H. Yashitake, *Colloids Surf. A. Physicochem. Eng. Aspects*, 2010, 36, 162). In addition, the organic functionalities are more homogeneously distributed during the co-condensation process, when compared with materials that are produced by the grafting method. This is especially so in the case of fabricating mesoporous structures in which organic functionalization of the center of the pores through grafting method may be impaired as a result of the pore blocking effect if the organosilanes react preferentially at pore openings. It is generally believed that periodic mesoporous organsilica particulates that are produced via hydrolysis and condensation reactions of bridged organosilica precursors have a higher degree of homogeneity of the organic functionalities (F. Hoffmann, M. Cornelius, J. Morell, M. Fröba, *Angew. Chem. Int. Ed.*, 2006, 45, 3216). Despite ample reports of such a method, the literature is sparse in the synthesis of silica-based hybrids containing dual functional groups.

A modified Stöber route for synthesizing silsesquioxane-silica hybrid (SqSH) particles by hydrolytic co-condensation of tetraethoxysilane (TEOS) with two trialkoxysilanes: 3-(trimethoxysilyl)propyldimethyloctadecyl ammonium chloride (SiQAC) and 3-methacryloxypropyltrimethoxysilane (3-MPTS), in one embodiment, without the use of an additional surfactant. The alkylammonium chain from SiQAC is responsible for its antimicrobial potential (Ahlström B., Thompson R. A., Edebo L., *APMIS*, 1999, 107, 318), and serves as a structure-directing agent (i.e., surfactant silane) during the co-condensation process Q. Huo, D. I. Margolese, G. D. Stucky, *Chem. Mater.*, 1996, 8, 1147). The dual roles of SiQAC as a surfactant silane and the contributor of the antimicrobial functionality eliminates the need for surfactant removal after synthesis, thereby avoiding the risk of destroying the other organic functionality (i.e., methacrylate groups from 3-MPTS, for example in one embodiment) during removal of surfactant by extractive or calcination methods. In this one-pot synthesis, the molar ratio of SiQAC and 3-MPTS was maintained at 1:1, while the molar ratio of TEOS varied from 1 to 32, resulting in silsesquioxane-silica hybrids (SqSHs) with overall molar ratios of 1:1:1, 1:2:1, 1:4:1, 1:8:1, 1:16:1 and 1:32:1. The sol-gel hydrolytic condensation product of TEOS was used as a comparative example (sol-gel silica).

Accordingly, in a first embodiment, the invention is directed to methods of preparing a silsesquioxane-silica hybrid, comprising:

hydrolytically co-condensing, in the presence of at least one ($C_1$-$C_3$)alcohol and a catalytic amount of an ammonium cation ($NH_4^+$), of a tetralkoxysilane of formula I:

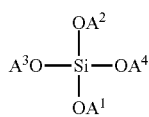

with a trialkoxysilane of formula II:

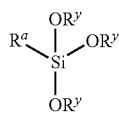

and with a trialkoxysilane of formula III:

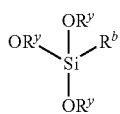

wherein said compound of formula II, said compound of formula I, and said compound of formula III are reacted in a molar ratio of about 1:1-32:1, respectively;

wherein:
$A^1$, $A^2$, $A^3$, and $A^4$ are each independently selected from the group consisting of H, $C_1$-$C_8$alkyl, and trifluoro-substituted ($C_1$-$C_8$)alkyl;

$R^a$ is independently a functional group comprising at least one curing group selected from the group consisting of acrylate, methacrylate, ($C_2$-$C_8$)alkenyl, glycidyloxy, epoxy, sulfonate, carboxylate, ester, amino, acrylamide, methacrylamide, isocyanato, amino acid, nucleic acid, and mercapto($C_1$-$C_6$)alkyl;

$R^b$ is independently

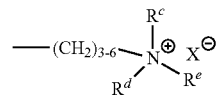

wherein:
$R^c$ is ($C_1$-$C_2$)alkyl;
$R^d$ is ($C_1$-$C_2$)alkyl or phenyl;
$R^e$ is ($C_6$-$C_{22}$)alkyl;

$X^-$ is an anion selected from the group consisting of chloride, bromide, fluoride, iodide, sulfonate, and acetate;

each $R^y$ is, independently, H, ($C_1$-$C_8$)alkyl, or trifluoro-substituted ($C_1$-$C_8$)alkyl.

In other embodiments, the invention is directed to the particles produced by the process. In certain embodiments, these particles have a substantially spherical morphology. In certain embodiments, these particles have a substantially ordered lamellar internal structure. In certain embodiments, these particles are mesoporous. In certain embodiments, these particles have the reacted residue of said trialkoxysilane of formula II and the reacted residue of said trialkoxysilane of formula III are substantially homogeneously distributed throughout said particle.

Other embodiments are directed to a plurality of particles, wherein each of said particles comprises:
a silsesquioxane-silica hybrid;
wherein each of said particles has a substantially spherical morphology;
wherein each of said particle has a substantially ordered lamellar internal structure;
wherein each of said particle is mesoporous; and
wherein the reacted residue of said trialkoxysilane of formula II and the reacted residue of said trialkoxysilane of formula III are substantially homogeneously distributed throughout each of said particle.

In yet other embodiments, the invention is directed to methods of preparing a polymer, comprising:
providing a plurality of particles described herein;
substantially fully hydrolyzing said particles to form a plurality of hydrolyzed particles; and
reacting said plurality of hydrolyzed particles with at least one co-monomer.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings:

FIG. 10A depicts mitochondrial succinic dehydrogenase activities of L-929 cells after incubating for 72 hours in DMEM containing SqSH or silica particles at different concentrations. Cytotoxicity of the SqSH particles on mammalian cells increased in a dose dependent manner. FIG. 10B depicts the concentration of different SqSH versions leading to 50% reduction in cell viability ($IC_{50}$) of the L-929 cells is illustrated here. $IC_{50}$ was determined by plotting the logarithm of particle concentration vs. reduction in cell viability. Note that sol-gel silica particles (predominantly inorganic in nature) are highly biocompatible and did not result in loss of cell viability reduction. A linear regression model was used to describe the relationship ($R^2$=0.982; P<0.05) between the $IC_{50}$ and the molar ratio of tetraethoxysilane to a trialkoxysilane.

DETAILED DESCRIPTION OF THE INVENTION

Figure 1:
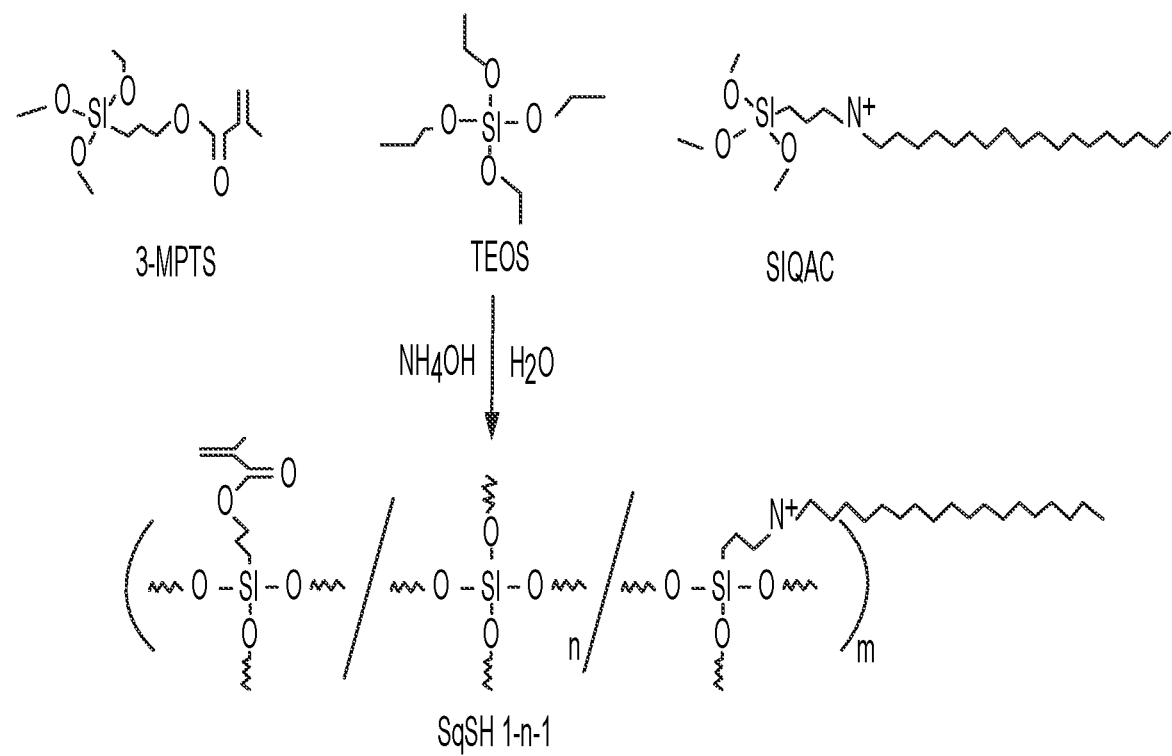
FIG. 1 shows a one-pot, co-condensation reaction scheme of one embodiment of the method of the invention.

As employed above and throughout the disclosure, the following terms, unless otherwise indicated, shall be understood to have the following meanings.

As used herein, the singular forms "a," "an," and "the" include the plural reference unless the context clearly indicates otherwise.

"Alkyl," as used herein, refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms or 1 to 6 carbon atoms ($C_1$-$C_6$) being preferred, and with from about 1 to about 4 carbon atoms. Alkyl groups include, but are not limited to, methyl, ethyl, n-propyl, isopropyl, n-butyl, isobutyl, t-butyl, n-pentyl, cyclopentyl, cyclopropyl, isopentyl, neopentyl, n-hexyl, isohexyl, cyclohexyl, cyclooctyl, adamantyl, 3-methylpentyl, 2,2-dimethylbutyl, and 2,3-dimethylbutyl. A branched alkyl group has at least 3 carbon atoms (e.g., an isopropyl group), and in various embodiments, has up to 6 carbon atoms, i.e., a branched lower alkyl group. A branched alkyl group has at least 3 carbon atoms (e.g., an isopropyl group), and in various embodiments, has up to 6 carbon atoms, i.e., a branched lower alkyl group.

"Alkenyl," as used herein, refers to an optionally substituted, singly unsaturated, straight, branched, or cyclic hydrocarbon having from about 2 to about 20 carbon atoms (and all combinations and subcombinations of ranges and specific numbers of carbon atoms therein), with from about 2 to about 8 carbon atoms or 2 to 6 carbon atoms ($C_2$-$C_6$) being preferred. Alkenyl groups include, but are not limited to, ethenyl (or vinyl), allyl, propenyl, butenyl, pentenyl, cyclopentenyl, hexenyl, and octenyl.

"Alkylenyl," as used herein, refer to the subsets of alkyl groups, as defined herein, including the same residues as alkyl but having two points of attachment within a chemical structure. Examples of ($C_1$-$C_6$)alkylenyl include methylenyl (—CH$_2$—), ethylenyl (—CH$_2$CH$_2$—), propylenyl (—CH$_2$CH$_2$CH$_2$—), and dimethylpropylenyl (—CH$_2$C(CH$_3$)$_2$CH$_2$—).

"Aryl," as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons ($C_6$-$C_{10}$) being preferred. Non-limiting examples include, for example, phenyl, naphthyl, anthracenyl, and phenanthrenyl.

As used herein, the terms "optionally substituted" or "substituted or unsubstituted" are intended to refer to the optional replacement of up to four hydrogen atoms with up to four independently selected substituent groups as defined herein. Unless otherwise specified, suitable substituent groups independently include hydroxyl, nitro, amino, imino, cyano, halo, thio, sulfonyl, aminocarbonyl, carbonylamino, carbonyl, oxo, guanidine, carboxyl, formyl, alkyl, perfluoroalkyl, alkylamino, dialkylamino, alkoxy, alkoxyalkyl, alkylcarbonyl, arylcarbonyl, alkylthio, aryl, heteroaryl, a heterocyclic ring, cycloalkyl, hydroxyalkyl, carboxyalkyl, haloalkyl, alkenyl, alkynyl, arylalkyl, aryloxy, heteroaryloxy, heteroarylalkyl, and the like. Substituent groups that have one or more available hydrogen atoms can in turn optionally bear further independently selected substituents, to a maximum of three levels of substitutions. For example, the term "optionally substituted alkyl" is intended to mean an alkyl group that can optionally have up to four of its hydrogen atoms replaced with substituent groups as defined above (i.e., a first level of substitution), wherein each of the substituent groups attached to the alkyl group can optionally have up to four of its hydrogen atoms replaced by substituent groups as defined above (i.e., a second level of substitution), and each of the substituent groups of the second level of substitution can optionally have up to four of its hydrogen atoms replaced by substituent groups as defined above (i.e., a third level of substitution).

"Mesoporous," as used herein, refers to a material containing pores with diameters about 2 nm to about 50 nm.

"Polydispersity index," as used herein, refers to the ratio of weight-average molecular weight to the number-average molecular weight (PDI=$M_w/M_n$).

"Molecular weight," as used herein, unless otherwise indicated, refers to the weight average molecular weight of a polymer as measured by gel permeation chromatography (GPC) against a polyacrylic acid standard.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

As used herein, the phrase "substantially" means have no more than about 10% difference between the target and actual level, preferably less than about 5% difference, more preferably, less than about 1% difference.

We have developed a facile method for synthesizing unique SqSH hybrid silica particles via a Stöber-like approach, with ordered lamellar structures with spherical morphology, without the use of additional surfactants. A scheme illustrating the influence of surfactant and formation of SqSH-silica hybrid nanospheres is shown in FIG. 1. This one-pot synthesis approach leads to the development of unique and useful antimicrobial hybrid silica particles with quaternary ammonium groups distributed within the entire particles, and therefore, non-leaching antimicrobial activities, as opposed to a grafting procedure, where thus type of functionality is present only along the particle surface. Moreover, antimicrobial activities are present irrespective of the degree of mesoscopic order of the hybrid silica particles. This synthesis approach may be further expanded by replacing the methacrylate functionality with other organofunctional moieties, thereby enabling the antimicrobial hybrid particles with tunable mechanical properties to be incorporated into different polymers/copolymers for a wide range of commercial applications. Likewise, this synthesis approach may be further expanded by replacing the antimicrobial functionality with other organofunctional moieties, thereby enabling the antimicrobial hybrid particles with tunable biological properties to be incorporated into different polymers/copolymers for a wide range of commercial applications.

Accordingly, in a first embodiment, the invention is directed to methods of preparing a silsesquioxane hybrids comprising:

hydrolytically co-condensing, in the presence of at least one ($C_1$-$C_3$)alcohol and a catalytic amount of an ammonium cation ($NH_4^+$), of a tetralkoxysilane of formula I:

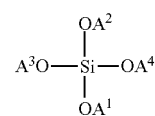

with a trialkoxysilane of formula II:

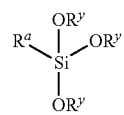

and with a trialkoxysilane of formula III:

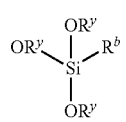

wherein said compound of formula II, said compound of formula I, and said compound of formula III are reacted in a molar ratio of about 1:1-32:1, respectively;

wherein:

$A^1$, $A^2$, $A^3$, and $A^4$ are each independently selected from the group consisting of H, $C_1$-$C_8$alkyl, and trifluoro-substituted ($C_1$-$C_8$)alkyl;

$R^a$ is independently a functional group comprising at least one curing group selected from the group consisting of acrylate, methacrylate, ($C_2$-$C_8$)alkenyl, glycidyloxy, epoxy, sulfonate, carboxylate, ester, amino, acrylamide, methacrylamide, isocyanato, amino acid, nucleic acid, and mercapto ($C_1$-$C_6$)alkyl;

$R^b$ is independently

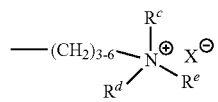

wherein:

$R^c$ is ($C_1$-$C_2$)alkyl;
$R^d$ is ($C_1$-$C_2$)alkyl or phenyl;
$R^e$ is ($C_6$-$C_{22}$)alkyl;
$X^-$ is an anion selected from the group consisting of chloride, bromide, fluoride, iodide, sulfonate, and acetate;

each $R^y$ is, independently, H, ($C_1$-$C_8$)alkyl, or trifluoro-substituted ($C_1$-$C_8$)alkyl. The silsesquioxane-silica hybrid compounds that are formed may be linear, branched, or star-shaped with the residues of compound I forming the backbone and the residues of compounds of formula II and formula III terminally located on the compounds.

In certain embodiments, said ($C_1$-$C_3$)alcohol is methanol, ethanol, propanol (n-propanol or isopropanol), or mixtures thereof. In certain embodiments, the ($C_1$-$C_3$)alcohol is ethanol.

In certain embodiments, said ammonium cation ($NH_4^+$) is derived from ammonium hydroxide, ammonium carbonate, ammonium chloride, ammonium nitrate, aqueous ammonia, or a mixture thereof. In certain embodiments, said ammonium cation ($NH_4^+$) is derived from ammonium hydroxide.

In certain embodiments, each $R^y$ is, independently, $R^y$ is, independently, H, methyl, ethyl, or propyl. In certain embodiments, each $R^y$ is H. In certain embodiments, each $R^y$ is methyl.

In certain embodiments, said siloxane of formula I is tetra($C_1$-$C_6$)alkoxysilane. In certain embodiments, said siloxane of formula I is tetramethoxysilane (TMOS), tetraethoxysilane (TEOS), tetrapropoxysilane (TPOS), or a mixture thereof. In certain embodiments, said siloxane of formula I is tetraethoxysilane (TEOS).

In certain embodiments, $R^a$ is acrylate, methacrylate, or vinyl, preferably methacrylate. In certain embodiments, $R^a$ is methacryloxypropyl.

In certain embodiments, said trialkoxysilane of formula II is 3-methacryloxypropyl trimethoxysilane (3-MPTS).

In certain embodiments, $R^y$ is H or ($C_1$-$C_2$)alkyl. Ethyl is preferred for certain dental and medical applications. In certain embodiments, $R^y$ is H.

In certain embodiments, $R^b$ is independently —($C_3$-$C_6$ alkylenyl)-(dimethyl)-($C_6$-$C_{22}$alkyl) quaternary ammonium chloride or —($C_3$-$C_6$ alkylenyl)-(methyl)-(phenyl)-($C_6$-$C_{22}$alkyl) quaternary ammonium chloride. In certain embodiments, $R^b$ is —($C_3$-$C_6$)alkylenyl-dimethyl-($C_{18}$alkyl) quaternary ammonium chloride, especially $R^b$ is —($C_3$ alkylenyl)-(dimethyl)-($C_{18}$alkyl) quaternary ammonium chloride, such Aegis 5700 or 5772 commercially available from Aegis or $R^b$ is —($C_3$-$C_6$)alkylenyl-methyl-phenyl-($C_6$-$C_{22}$alkyl) quaternary ammonium chloride, which may be prepared by N-alkylation of N-hexylaniline in a two-step process where N-hexylanlysis is reacted with 3-chloropropyl)triethoxysilane to yield a tertiary amine which then is further quarternized in the second step by reacting with iodomethane, such as described in Saif, et al., Langmuir, 2009, 25, 377-379.

In certain embodiments, $R^b$ is

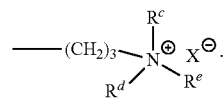

In certain embodiments, $R^c$ is methyl.
In certain embodiments, $R^d$ is methyl.
In certain embodiments, $R^e$ is octadecyl.
In certain embodiments, $X^\ominus$ is $Cl^-$.
In certain embodiments, said trialkoxysilane of formula III is 3-(trimethoxysilyl)propyldimethyloctadecyl ammonium chloride (SiQAC).

In certain embodiments, said method is conducted substantially free of a separate surfactant other than said compound of formula II.

In certain embodiments, said compound of formula II, said compound of formula I, and said compound of formula III are reacted in a molar ratio selected from the group consisting of 1:1:1, 1:2:1, 1:4:1, 1:8:1, 1:16:1, 1:32:1, and mixtures thereof, respectively.

In other embodiments, the invention is directed to the particles produced by the process. In certain embodiments, these particles have a substantially spherical morphology. In certain embodiments, these particles have a substantially ordered lamellar internal structure. In certain embodiments, these particles are mesoporous. In certain embodiments, these particles have the reacted residue of said trialkoxysilane of formula II and the reacted residue of said trialkoxysilane of formula III are substantially homogeneously distributed throughout said particle.

Other embodiments are directed to a plurality of particles, wherein each of said particles comprises:
a silsesquioxane-silica hybrid;
wherein each of said particles has a substantially spherical morphology;
wherein each of said particle has a substantially ordered lamellar internal structure;
wherein each of said particle is mesoporous; and
wherein the reacted residue of said trialkoxysilane of formula II and the reacted residue of said trialkoxysilane of formula III are substantially homogeneously distributed throughout each of said particle.

In certain embodiments, said plurality of particles has an average particle size of about 50 nm to about 2000 nm, preferably about 250 nm to about 1000 nm. In certain embodiments, said plurality of particles has a polydispersity index of about 1 to about 20. In certain embodiments, the $M_w$ is about 20,000 to about 200,000.

In yet other embodiments, the invention is directed to methods of preparing a polymer, comprising:
providing a plurality of particles described herein;
substantially fully hydrolyzing said particles to form a plurality of hydrolyzed particles; and
reacting said plurality of hydrolyzed particles with at least one co-monomer.

In another embodiment, the invention is directed to kits, comprising:
 a plurality of particles described herein;
 at least one polymerization initiator;
 optionally, at least one synergist;
 optionally, at least one filler; and
 optionally, at least one co-monomer.

In other embodiments, the invention is directed to compositions, comprising:
 at least one filler;
 a plurality of particles described herein;
 wherein said plurality of particles is sorbed on said filler.

In other embodiments, the compositions, further comprise:
 at least one natural rubber, synthetic rubber, or a combination thereof.

In another embodiment, the compositions, further comprise:
 at least one first polymer selected from the group consisting of thermoplastic polymer, thermosetting polymer, and mixtures thereof.

In yet other embodiments, the invention is directed to polymeric articles, comprising:
 said compositions described herein, said particles described herein or a polymerized residue of said particles described herein.

In further embodiments, the invention is directed to coating materials, comprising:
 said compositions described herein, said particles described herein or a polymerized residue of said particles described herein.

In other embodiments, the invention is directed to compositions comprising:
 the polymerized residue of said particles described herein.

In another embodiment, the invention is directed to toothpastes, comprising:
 said compositions described herein or said particles described herein.

In other embodiments, the invention is directed to mouthwashes,
 comprising:
 said compositions described herein or said particles described herein.

In yet other embodiments, the invention is directed to contact lenses, comprising:
 said compositions described herein, said particles described herein or a polymerized residue of said particles described herein.

In other embodiments, the invention is directed to the products produced by the processes and methods described herein.

Another embodiment of this invention is a water solution of said compositions described herein, said particles described herein or a polymerized residue of said particles described herein.

Still another embodiment of this invention is a water-alcohol solution of said compositions described herein, said particles described herein or a polymerized residue of said particles described herein.

Yet another embodiment is the use of the material described herein as fillers for adhesive (primer) and the use of the material described herein in commercial adhesives used in dentistry.

Still another embodiment is the use of a material described herein as an additive (filler) to dental compositions for adhesion of the dental composition to a tooth. Other embodiments include the use of a material described herein as fillers for plastic bags, polyethylene films, toothpastes, and any other application requiring a filler polymer, especially one that is antimicrobial.

In addition, the materials of this invention can act as tooth desensitizers when placed on a tooth, and still further, this material can be added to filler material for teeth, especially filling materials such as siloxanes, glass ionomers, methacrylates, and silver amalgams.

In still other embodiments, the materials of the invention may be used in contact lenses as the primary material or as a secondary material.

In certain embodiments, the compositions described herein further comprise at least one natural rubber, synthetic rubber, or a combination thereof. In certain other embodiments, the compositions further comprise at least one first polymer selected from the group consisting of thermoplastic polymer, thermosetting polymer, and mixtures thereof.

In certain embodiments, the compositions comprising said compositions described herein, said particles described herein or a polymerized residue of said particles described herein, further comprise at least one first polymer selected from the group consisting of thermoplastic polymer, thermosetting polymer, and mixtures thereof.

Suitable thermoplastic polymers for use in the compositions of the invention include, but are not limited to, polyethylene, polypropylene, polyvinyl chloride, polyester, acrylic, methacrylic, or a copolymer or mixture thereof.

Suitable thermosetting polymers for use in the compositions of the invention include, but are not limited to, epoxy, polyester, alkyd, diallyl phthalate, melamine, polybutadiene, phenolic, silicone, urea, urethane, imide, or a mixture thereof.

In certain embodiments, the compositions described herein, the particles described herein or a polymerized residue of the particles described herein are in the form of a powder. In certain embodiments, the compositions of the invention are in the form of a master batch. A "master batch," as used herein, is a product in which additives are dispersed (usually well dispersed) in a carrier material that is compatible with the main polymer or plastic in which it will be let down and may be supplied in a granule, a pellet, or a powder form. In certain embodiments, the compositions of the invention further comprise a second polymer that is the same or different from the first polymer.

In certain embodiments, the compositions described herein, the particles described herein or a polymerized residue of the particles described herein, with or without filler, further comprise at least one first polymer wherein said first polymer is:
 acrylonitrile-butadiene-styrene;
 acetal;
 acrylic;
 methacrylic;
 cellulosic (such as acetate, butyrate, ethyl cellulose, nitrate, propionate);
 ethylene copolymers (such as ethylene methyl acrylate, ethylene-n-butyl acrylate, ethylene vinyl acetate, ethylene methyl acrylic acid, ethylene acrylic acid, ethylene ethyl acrylate);
 fluoropolymer (such as fluorinated ethylene propylene, polytetrafluoroethylene, chlorotrifluoroethylene, polyvinylidene fluoride, ethylene tetrafluoroethylene-ethylene chlorotrifluoroethylene);
 nylon (such as nylon 6/6, 6, 6/10, 8, 12, and copolymers thereof);
 polyarylate;
 polyarylsufone;

polybutylene;
polycarbonate;
polycarbonate-acrylonitrile-butadiene-styrene alloy;
polyesters (such as polyethylene terephthalate, polybutylene terephthalate, polytetramethylene terephthalate, and copolymers thereof);
polyetheretherketone;
polyetherimide;
polyethersulfone;
polyethylene (low density, linear low density, high density, high molecular weight);
ionomer;
polymethylpentene;
polyphenylene oxide;
polyphenylene sulfide;
polyimide;
polyproplylene (general purpose, impact copolymers, random copolymers);
polystyrene (general purpose, high impact, medium impact);
polysulfone;
polyurethane;
polyvinyl chloride;
chlorinated polyvinyl chloride;
polyvinyl chloride-acrylic;
polyvinyl chloride-acrylonitrile-butadiene-styrene;
styrene acrylonitrile;
styrene maleic anhydride;
thermoplastic elastomer;
thermoplastic vulcanizate; or
a copolymer or a mixture thereof.

In certain embodiments, the compositions described herein, the particles described herein or a polymerized residue of the particles described herein and filler further comprise at least one thermoplastic polymer, thermosetting polymer, or a combination thereof. Suitable thermoplastic polymers include, but are not limited to, polyethylene, polypropylene, polyvinyl chloride, polyesters, and the like, copolymers and mixtures thereof.

In certain embodiments, the compositions described herein, the particles described herein or a polymerized residue of the particles described herein, with or without filler, are useful as polymeric articles, such as film, sheet, container, foam container, bottle, crate, plastic parts, toys, pipe, foam insulation, panel, plastic lumber, or the like. In certain embodiments, the polymeric article is prepared by blown film, cast film, extrusion (such as profile extrusion, sheet extrusion, and foam extrusion), roto-molding, injection molding, blow molding, foamed, coating, or a combination thereof or the like.

In certain embodiments, the compositions described herein, the particles described herein or a polymerized residue of the particles described herein, with or without filler, are useful as toothpaste, mouthwash, contact lenses (for example in heat curable systems with HEMA and a small amount of ethyleneglycol methacrylate), artificial nails and adhesives therefor, and the like.

The compositions described herein, the particles described herein or a polymerized residue of the particles described herein may be used to increase the contact angle (and hence increase the surface energy) of compositions into which they are incorporated. Thus, the compounds of the invention are useful in methods of increasing the printability and/or dyeability of a polymeric composition. For example, this would lead to better print quality and permitting use of environmentally-friendly water-based inks in the place of solvent-based inks. Such methods comprise incorporating said compositions described herein, said particles described herein or a polymerized residue of said particles described herein into a polymeric composition, either as a separate component or as a residue in the polymer itself (by polymerizing with at least one co-monomer).

The compositions described herein, the particles described herein or a polymerized residue of the particles described herein may be used to increase the hydrophilicity, improve antistatic properties, and reduce surface resistivity (by attracting water) of the compositions into which they are incorporated. Such methods comprise incorporating the compositions described herein, the particles described herein or a polymerized residue of the particles described herein into a polymeric composition, either as a separate component or as a residue in the polymer itself (by polymerizing with at least one co-monomer).

The present invention is further defined in the following Examples, in which all parts and percentages are by weight, unless otherwise stated. It should be understood that these examples, while indicating preferred embodiments of the invention, are given by way of illustration only and are not to be construed as limiting in any manner. From the above discussion and these examples, one skilled in the art can ascertain the essential characteristics of this invention, and without departing from the spirit and scope thereof, can make various changes and modifications of the invention to adapt it to various usages and conditions.

EXAMPLES

Materials and Methods

Chemicals and reagents: Tetraethoxysilane (TEOS), 3-(trimethoxysilyl)propyldimethyloctadecyl ammonium chloride (SiQAC), 3-methacryloxypropyltrimethoxysilane (3-MPTS), ammonium hydroxide solution (28-30% $NH_3$), triethylene glycol dimethacrylate (TEGDMA), ethyl(4-dimethylamino)benzoate (EDMAB) and camphorquinone (CQ) were purchased from Sigma-Aldrich (St Louis, Minn., USA) and used without further purification. The SiQAC was supplied at 72 weight % in methanol. 2,2-bis[4-(2-hydroxy-3-methacryloxypropoxy)phenyl]propane (bis-GMA) was a gift from Esstech, Inc. (Essington, Pa., USA).

Co-Condensation Procedure

The molar ratio of SiQAC and 3-MPTS was maintained at 1:1, while the molar ratio of TEOS varied from 1 to 32, resulting in silsesquioxane-silica hybrids (SqSHs) with overall molar ratios of 1:1:1, 1:2:1, 1:4:1, 1:8:1, 1:16:1 and 1:32:1 (FIG. 1). The sol-gel hydrolysis/condensation product of TEOS was used as control (sol-gel silica). Co-condensation was processed via a modified Stöber route W. Stöber, A. Fink, E. Bohn, J. Colloid Interface Sci., 1968, 26, 62): 16 mL of ethanol, 25 mL of deionized water, and 9 mL of $NH_4OH$ solution were mixed and stirred at 1200 rpm. To this solution, 5 mL of TEOS, or SiQAC-3-MPTS-TEOS premixed in 45 mL of ethanol, was rapidly added. After 1 minute, the stirring speed was reduced to 350 rpm. The reaction was maintained at room temperature for 2 hours. The product was then centrifuged and washed with copious amounts of water and ethanol. The procedures were repeated three times before the reaction products were dried under vacuum. The yield varied from 55 to 86 weight %. The yield of the SqSHs varied with respect to the molar ratio of the trialkoxysilane (i.e., high proportion of trialkoxysilane decreased the yield rate). Due to the different hydrolysis and condensation kinetics of the structurally different precursors, a relatively higher proportion of trialkoxysilane in the reaction mixture favors homocondensation reactions of the trialkoxysilanes, at the expense of co-condensation with the inorganic silica precursor (TEOS). This accounts for the wide variety in yields among the SqSHs prepared with different molar ratios of the precursors after ethanol extraction of the homocondensation reaction products.

Attenuated total reflection-Fourier transform infrared (FTIR) spectroscopy

Infrared spectra were recorded between 4,000-400 $cm^{-1}$ using a Fourier-transform infrared spectrometer (Nicolet 6700, Thermo Scientific, Waltham, Mass., USA) with an attenuated total reflection (ATR) set up at a resolution of 4 $cm^{-1}$ and averaging 32 scans per spectrum.

Nuclear Magnetic Resonance (NMR) Characterization

The structures of SqSHs and sol-gel silica were characterized by $^{29}Si$ solid-state NMR at ambient temperature using a 270 MHz spectrometer (JEOL, Tokyo, Japan) equipped with a 7 mm Magic Angle Spinning (MAS) probe. Spectra were acquired in the $^{1}H \rightarrow ^{29}Si$ cross polarization (CP) mode, using a MAS frequency of 4 kHz, with a 45 degree pulse angle of 5 psec. The $^{1}H$ Larmor frequency for $^{29}Si$ was 53.76 MHz. Chemical shifts were referenced to external tetramethylsilane (TMS) at 0 ppm.

Thermogravimetric Analysis (TGA)

TGA was performed with a Q500 thormogravimetric analyzer (TA Instruments, New Castle, Del., USA). Approximately 40 mg of dried particles (SqSHs or sol-gel silica) was placed in individual platinum pans and heated at a rate of 10° C./min to 1000° C. in atmospheric air. The data were analyzed using the Universal Analysis 2000 software (TA Instruments) and expressed as weight vs temperature as well as derivative weight vs temperature.

Powder X-Ray Diffraction (XRD)

X-ray diffraction (Rigaku America, Woodlands, Tex., USA) of the non-sintered particles was performed using Ni-filtered Cu Kα radiation (30 KeV, 20 mA), in the 2θ range of 1-30°, with a scan rate of 4°/min, and a sampling interval of 0.02°. The determination of d-spacing values was based on Bragg-Brentano geometry.

Electron Microscopy

Dried particles sputter-coated with gold/palladium were examined using a field emission-scanning electron microscope (XL-30 FEG; Philips, Eindhoven, The Netherlands) operating at 10-15 kV. Dried particles were embedded in epoxy resin and cut into 70-90 nm thick sections. Unstained sections were examined using a JSM-1230 transmission electron microscope (JEOL, Tokyo, Japan) at 110 kV. Selected area electron diffraction (SAED) was performed to identify the crystallinity of the SqSH particles.

Scanning Transmission Electron Microscopy-Energy Dispersive X-Ray Analysis (STEM-EDX)

Elemental analysis of representative SqSH 1:8:1 and 1:32:1 was performed on unstained thin sections prepared previously for TEM using a Tecnai G2 STEM (FEI, Hillsboro, Oreg., USA) at 200 kV. Spectrum acquisition and elemental mapping were conducted using an Oxford Instruments *INCA* x-sight detector. Images were collected with a Gatan 1K×1K CCD camera. Elemental mappings were acquired with the FEI TIA software using a spot dwell time of 300 msec. As each 250×250 pixel mapping required 7 hours to complete, drift correction was performed after every 30 images.

Nanoindentation

Cold-polymerized epoxy resin with embedded SqSH or sol-gel silica particles was sectioned with a water-cooled diamond-impregnated blasé to expose the particles along the flat resin surface. Mechanical properties of the specimens were evaluated by quasi-static indentation using a nanoindenter (Hysitron Tribinderter 900, Minneapolis, Minn., USA) with a 100 nm radius cono-spherical diamond tip indenter. A standard trapezoidal profile was used including a maximum load of 100 mN, indentation hold time of 5 sec, and loading and unloading rates of 20 mN/sec. An initial offset load of 10 mN was used for identifying contact and initialize the indentation process. The load-displacement curves generated for the individual indentations were corrected for the offset force. Six indentations were performed to characterize the mechanical behavior of each SqSH or sol-gel silica control (N=6). Reduced modulus and hardness (in GPa) were calculated based on the Oliver-Pharr method for nanoindentation testing (W. C. Oliver, G. M. Pharr, *J. Mater. Res.*, 1992, 7, 1564). Data were analyzed using one-way ANOVA with Tukey's multiple comparison at α=0.05.

Antimicrobial Activities of Bis-GMA/TEGDMA Resin Containing SqSH

A bis-GMA/TEGDMA light-polymerizable resin blend (composition: 70 weight % bis-GMA, 28.5 weight % TEGDMA, 1 weight % EDMAB and 0.5 weight % CQ) was used to mix with 50 weight % SqSH particles in a centrifugal mixing device at 3200 rpm for 60 seconds (DAC 150 Speedmixer; FlackTek Inc., Landrum, S.C., USA). Bis-GMA/TEGDMA resin without any SqSH was used as control. Polymerization of these resins was achieved by photocuring with visible light in the wavelength range of 410-500 nm. With a Teflon mold and Mylar sheets covering both sides, polymerized resin disks (6±0.1 mm diameter, 1 t 0.1 mm thick) were fabricated.

*Streptococcus mutans* ATCC 35668 (ATCC, Manassas, Va., USA) and *Actinomyces naeslundii* ATCC 12104 were cultured in Brain Heart Infusion (BHI) broth (Difco, Becton-Dickinson and Co., Sparks, Md., USA), supplemented with 50 mM sucrose (pH 7.2). *Candida albicans* ATCC 90028 was cultured in Yeast Nitrogen Base (YNB; Difco) supplemented with 50 mM glucose (pH 7.2). Harvested cells were re-suspended in 100 mL of the respective growth medium, and adjusted to a concentration of $10^7$ CFU/mL before use. Each microbe was used individually for the formation of single-species biofilms on salivary pellicle-coated resin disks inside an oral biofilm reactor. After the formation of biofilms on acrylic surfaces, half of the disks from each group were transferred carefully into separate microtubes containing 4 mL of phosphate buffered saline (PBS; 0.01 mM, pH 7.3), avoiding any disturbances to the biofilms. Fifty mL of 1 mg/mL solution of 2,3-bis-(2-methoxy-4-nitro-5-sulfophenyl)-2H-tetrazolium-5-carboxanilide (XTT; Sigma-Aldrich) was then added to each microtube, together with 4 μL of 1 mM menadione (Sigma-Aldrich). The solutions were mixed gently, covered with aluminum foil, and incubated for 5 hours at 37° C. After incubation, the solution was transferred to a new microtube and centrifuged at 4000 rpm for 10 minutes at 4° C. The supernatant was placed in a 96-well plate and read at 492 nm using a spectrophotometer (Victor, R & D systems, Minnesota, USA).

The rest of the disks from each group were placed carefully in separate microtubes containing 1 mL of PBS and vortexed (Maxi Mix vortex mixer, Thermo Scientific, Waltham, Mass., USA) for 2 min at high speed to detach the biofilm. Ten-fold serial dilutions were generated in PBS (0.01 mM, pH 7.3), and each dilution was plated (50 μL aliquots) onto Sabouraud Dextrose Agar plates for *C. albicans*, and Brain Heart Infusion agar plates for *S. mutans* and *A. naeslundii*. The plates were incubated at 37° C. for 48 hours in an aerobic chamber for *C. albicans* and anaerobic chamber for *S. mutans* and *A. naeslundii*. After incubation, the colony forming counts (CFU) per resin disk were counted manually. Data were analyzed using one-way ANOVA with Tukey's multiple comparison at α=0.05.

Cytotoxicity

The cytotoxicity of SqSHs and sol-gel silica was investigated using a mouse fibroblast cell line (L-929). The growth medium for L-929 consisted of Dulbecco's Modified Eagle's Medium (DMEM, Lonza, Wakersville, Md., USA) and 10% fetal bovine serum (Gibco; Invitrogen Corp., Carlsbad, Calif., USA), supplemented with 2 mM L-glutamine, 100 U/mL penicillin, and 100 µg/mL streptomycin. The cells were plated in a 96-well plate at a density of 5000 cells/cm$^2$, in 200 µL of the growth medium, and incubated at 37° C. in a humidified 5% $CO_2$ atmosphere. After 24 hours, pre-confluent cells were washed twice with serum or antibiotics free DMEM and further incubated in DMEM containing SqSH or silica particles at different concentrations. Cells incubated in growth medium without particles were used as the blank control.

The final SqSH or silica dispersions in DMEM were prepared immediately before use by serial dilution (i.e., 2, 5, 25, 125, 625, and 3125 folds) of the stock suspension (ca. 883 µg/mL) with intense vortexing.

Succinic dehydrogenase (SDH) activity of the cells was determined using 3-(4,5-dimethylthiazol-2-yl)-2,5-diphenyltetrazolium bromide (MTT) assay. The retrieved cells were incubated in MTT-succinate solution for 60 min and fixed with Tris-formalin. The formazan product was dissolved in-situ using DMSO and absorbance was recorded using a microplate reader at 562 nm. Results were determined as a percentage of mean control values. The half-maximal inhibitory concentration ($IC_{50}$) was defined as the concentration of SqSH or silica particles leading to a 50% reduction in L-929 cell viability A. M. Chen, M. Zhang, D. Wei, D. Stueber, O. Taratula, T. Minko, H. He, Small, 2009, 5, 2673). It was determined by linear regression analysis of the logarithmic derivative of particle concentration vs reduction of cell viability using SPSS 16.0 (SPSS Inc., Chicago, Ill., USA).

Synthesis of SqSH Particles by Hydrolytic Co-Condensation and Characterization

An issue that confronts silane-based co-condensation reactions is homocondensation of the trialkoxysilanes (H. Yoshitake, New J. Chem., 2005, 29, 1107). Thus, the reaction products of the sol-gel reactions were subjected to multiple washings in ethanol prior to analyses to remove unreacted reagents. Attenuated total reflection-Fourier transform infrared (ATR-FTIR) spectroscopy validates the presence both the methacrylate group at 1690-1714 cm$^{-1}$ (C=O), 1637 cm$^{-1}$ (C=C), 1305 cm$^{-1}$ (C—CO—O), 1295 cm$^{-1}$ (C—CO—O) (S. K. Medda, D. Kundu, G. De, J. Non-Cryst. Solids, 2003, 318, 149), 815 cm$^{-1}$ (C=C)) and the alkylammonium chain (1373 cm$^{-1}$ (C—N)(S. Köytepe, T. Seckin, N. Kivrilcim, H. 1. Adigüzel, J. Inorgnomet. Polym., 2008, 18, 222) in the sol-gel reaction products (FIG. 2e), thereby confirming the co-condensation of TEOS with 3-MPTS and SIQAC in the multiple-rinsed reaction products.

Figures 2A, 2B:
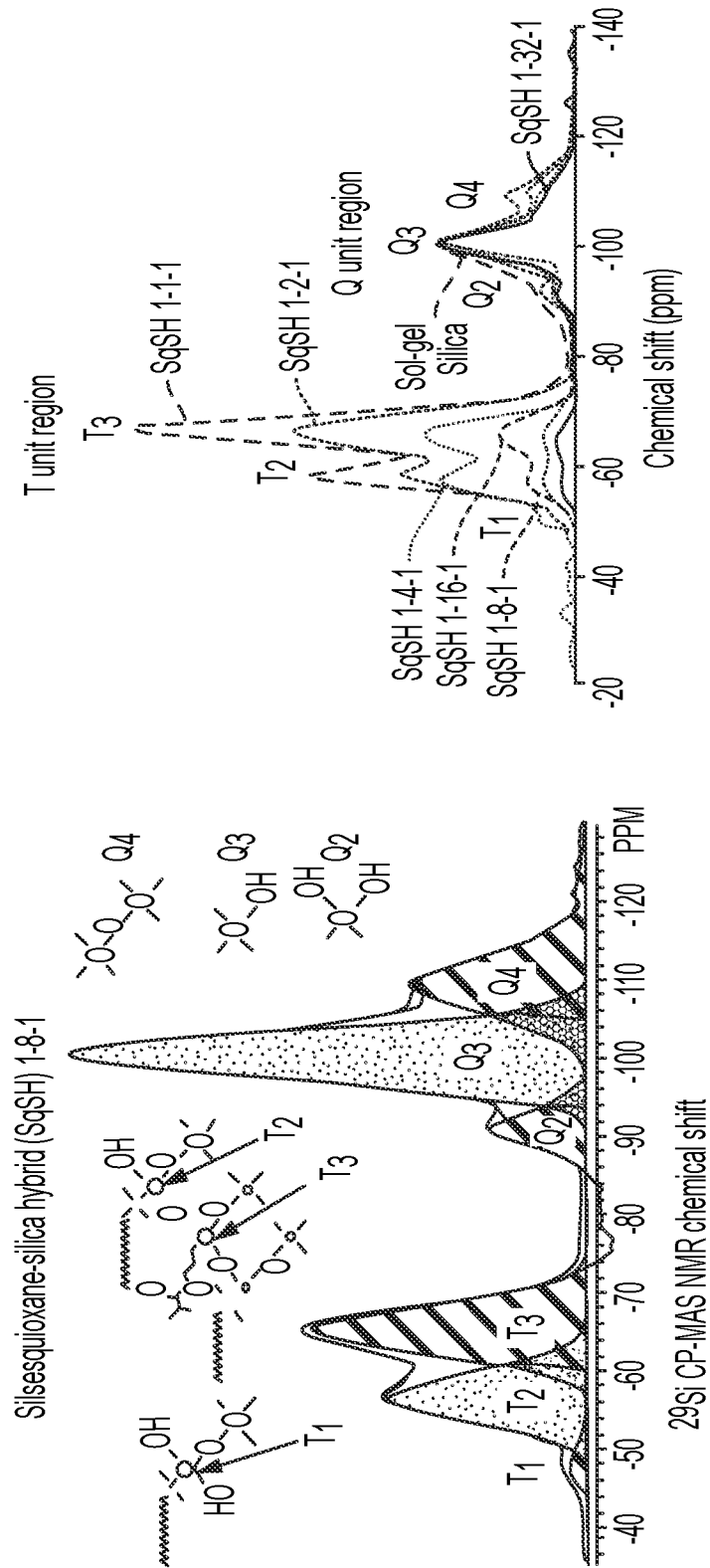
FIGS. 2a to 2d show $^{29}$Si cross polarization-magic angle spinning nuclear magnetic resonance spectroscopy (CP-MAS NMR).
Figure 2D:
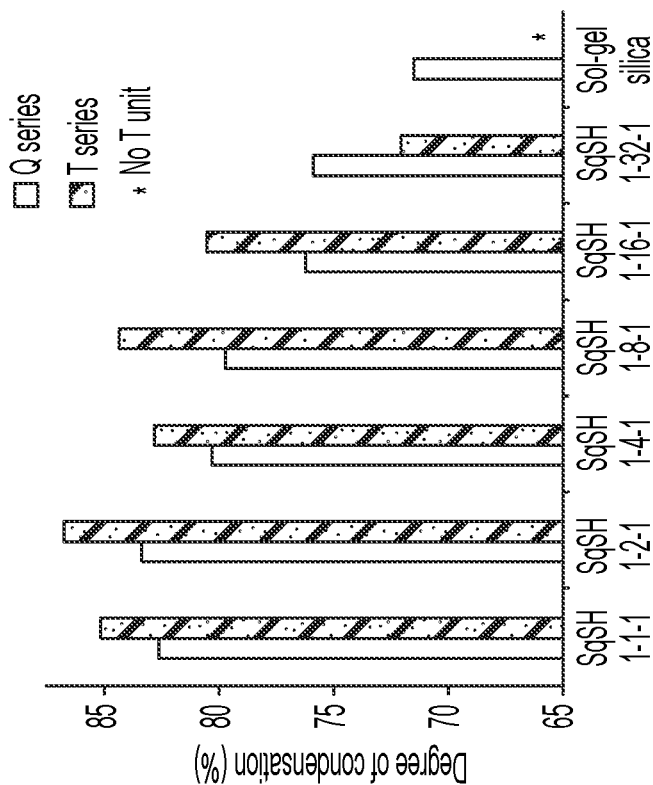
Figure 2C:
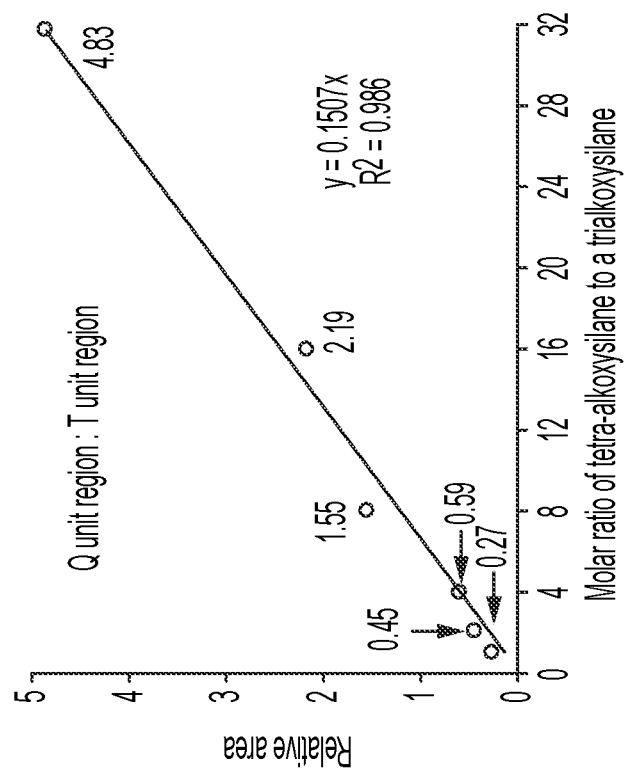
Figure 2E:
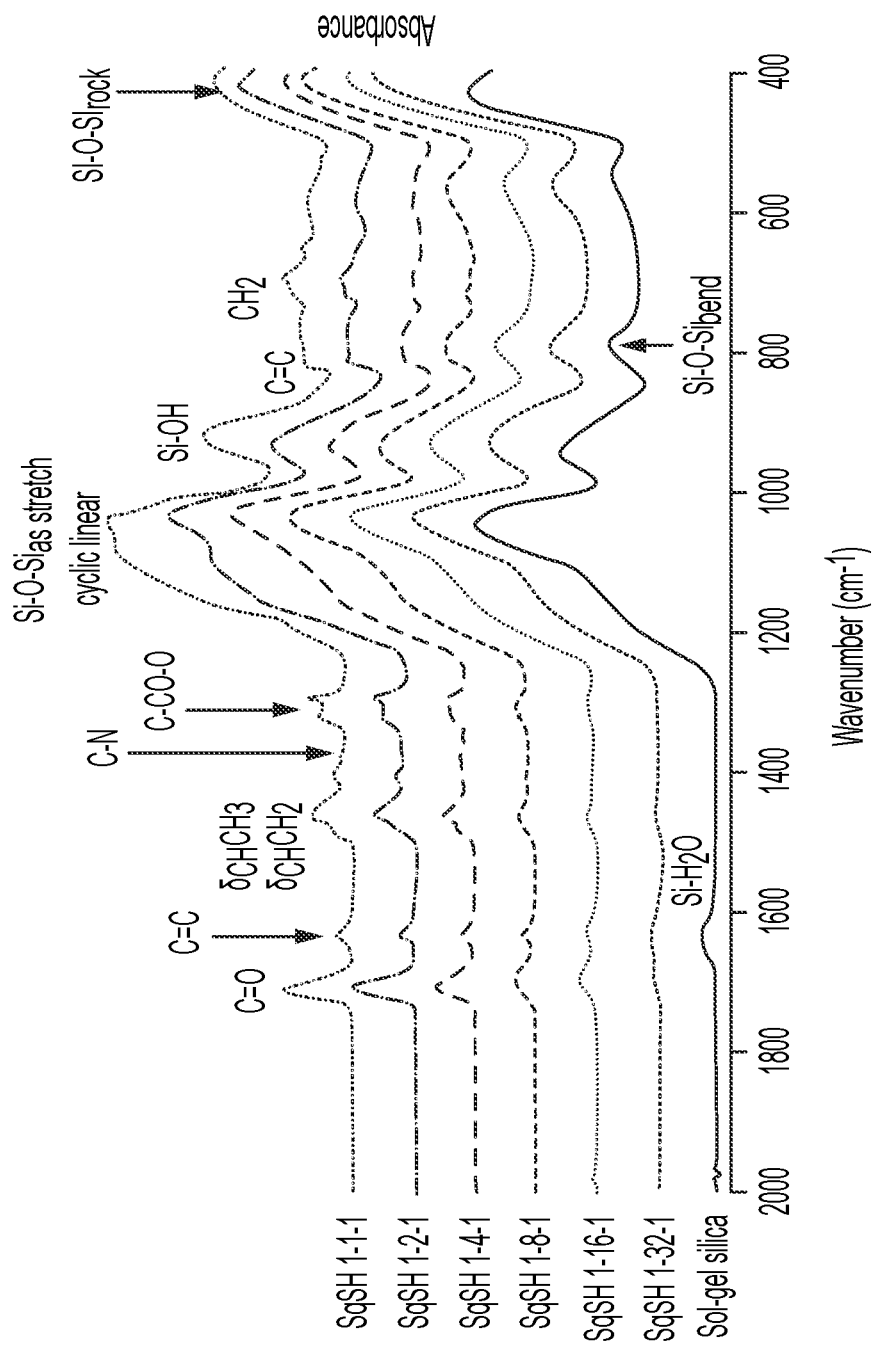
FIG. 2e shows the Fourier transform infrared spectroscopy (FTIR) of silsesquioxane-silica hybrids (SqSHs) of one embodiment of the invention and a comparative sol-gel silica. The broad absorbance band from ~1000-1100 cm$^{-1}$ is assigned to asymmetric stretching vibration of Si—O—Si groups. With higher organic content in the hybrid (SqSH 1:1:1 and SqSH 1:2:1), two separate peaks are present, indicating two components from Si—O—Si groups in cyclic (~1080 cm$^{-1}$) and linear (~1040 cm$^{-1}$) structures. Cyclic structure of Si—O—Si is considered to be more condensed than linear Si—O—Si. This is consistent to $^{29}$Si NMR results showing that SqSH 1:1:1 and SqSH 1:2:1 have higher degrees of condensation (FIG. 2d). The peaks at ~792 cm$^{-1}$ and ~430 cm$^{-1}$ are assigned to Si—O—Si bending and rock vibration, respectively. The peak at ~935 cm$^{-1}$ is derived from silanol group (SiOH). The absorbance band peaking at 1633 cm$^{-1}$ is assigned to deformational vibration of absorbed water molecules (Si—H$_2$O). The presence of methacrylate from 3-MPTS are confirmed by peaks at 1690-1714 cm$^{-1}$ (C=O), 1637 cm$^{-1}$ (C=C), 1305 cm$^{-1}$ (C—CO—O), 1295 cm$^{-1}$ (C—CO—O), and 815 cm$^{-1}$ (C=C). The C—N stretch vibration peaking at 1373 cm$^{-1}$ validates the presence of SiQAC.
Figure 5A:
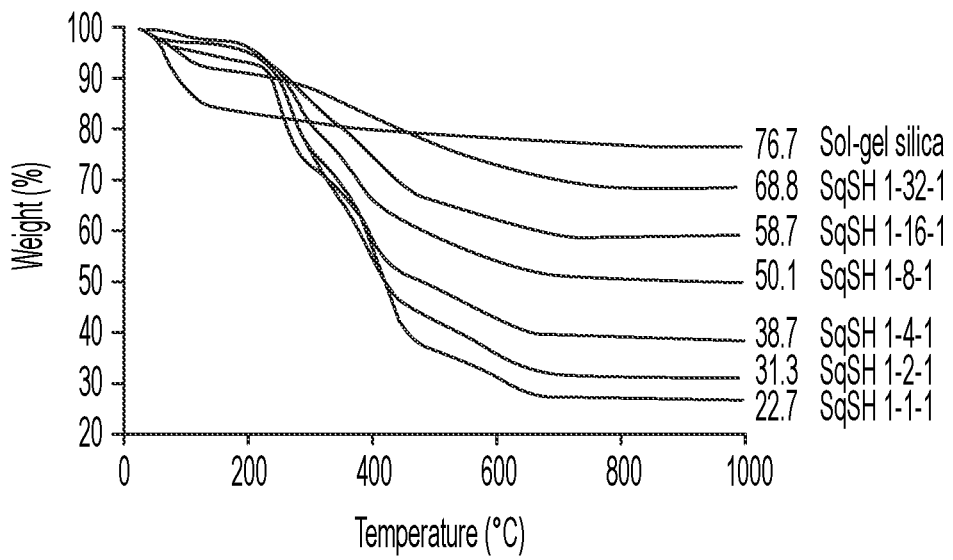
FIGS. 5 a to c show thermogravimetric analysis (TGA) of one embodiment of the invention and a comparative sol-gel silica at a rate of 10° C./min from ambient temperature to 1000° C. in atmospheric air. (a) Thermograms for SqSHs and sol-gel silica. The residual mass that remains after reaching at 700° C. is due to residual inorganic silica content. The weight percentage of remaining silica in SqSHs 1:1:1, 1:2:1, 1:4:1, 1:8:1, 1:16:1, 1:32:1 and comparative sol-gel silica are 22.7, 31.3, 38.7, 50.1, 58.7, 68.8, and 76.7 weight %, respectively. (b) Logarithmic regression model provides an excellent fit ($R^2$=0.987; P<0.01) for the relation between the residual weight percentage and the molar ratio of tetraethoxysilane to a trialkoxysilane. (c) Derivative weight loss curves for SqSHs and sol-gel silica. For the peak below 100° C. (A), the highest was seen with sol-gel silica while the lowest peak was seen with SqSH 1:1:1. This indicates that there is more water molecules inside the sol-gel silica network. The overall peak intensity of the derivative weight plots increases with the increased composition of organosilane in SqSHs. The two peaks (B and C) from 200 to 420° C. indicate the decomposition of organic constituents (D. S. Bag, K. U. Rao, J. Appl. Poly. Sci. 2010, 115, 2352), representing two-stage decomposition of organic substances from SqSHs (W. Xie, Z. Gao, W.-P. Pan, D. Hunter, A. Singh, R. Vaia, Chem. Mater. 2001, 13, 2979). The peaks (D) above 600° C. are attributed to further condensation of the silanol groups in the bulk silicate network.
Figure 5B:
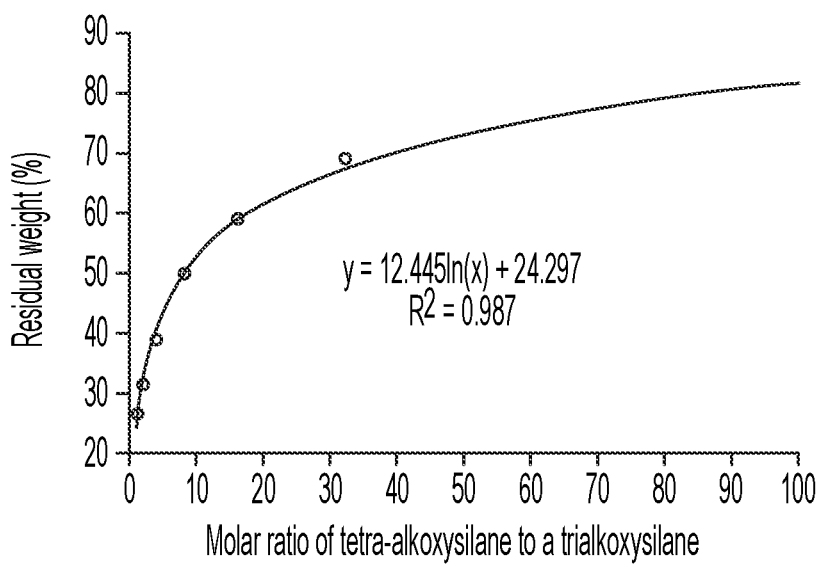
Figure 5C:
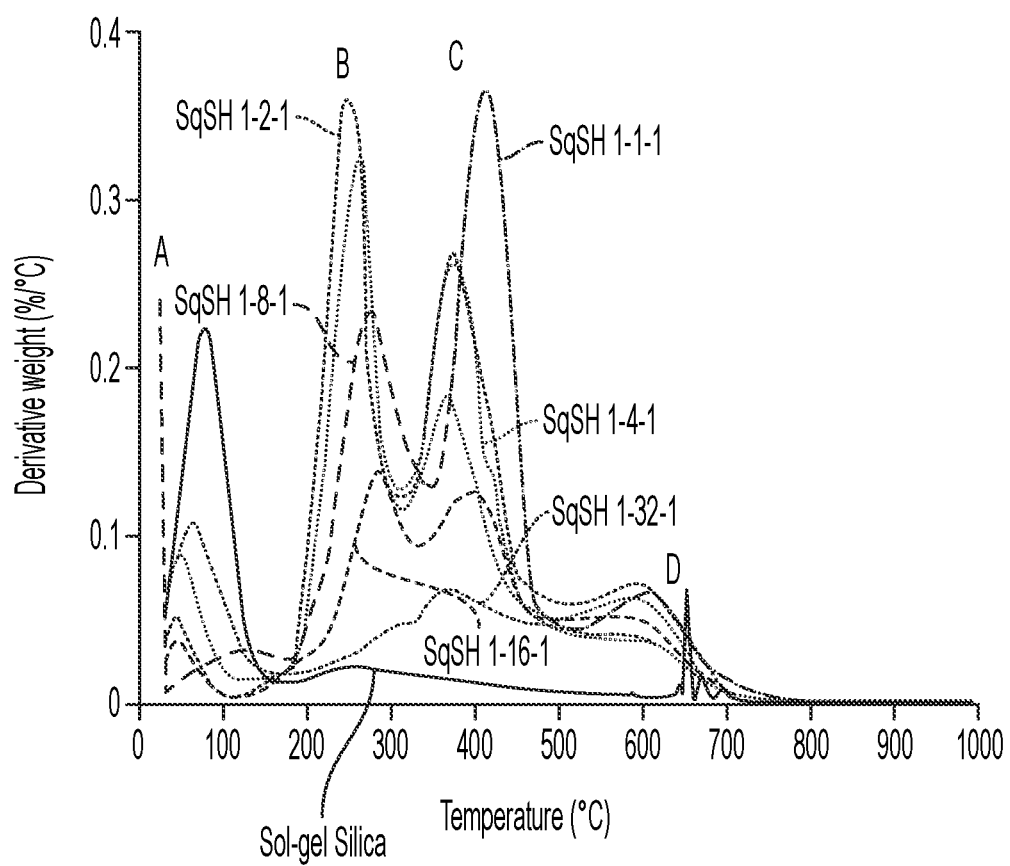

Using $^{29}$Si cross polarization-magic angle spinning nuclear magnetic resonance spectroscopy (CP-MAS NMR), two different units were delineated from the NMR spectrum, providing information on the connectivity of the silica network (C. Bonhomme, C. Coelho, N. Baccile, C. Gervais, T. Azaïs, F. Babonneau, Acc. Chem. Res., 2007, 40, 738): $T_n$:RSKOH)$_{(3-n)}$(OSi)$_n$, and $Q_n$:Si(OH)$_{(4-n)}$(OSi)$_n$ (FIG. 2a). As shown by the overlay of the NMR spectra of SqSHs and inorganic sol-gel silica synthesized by the Stöber method, with all spectra normalized to the $Q_3$ unit, the relative areas of the T unit region increase linearly as a function of the feed ratio of trialkoxysilanes (3-MPTS and SiQAC) to TEOS (FIGS. 2b and 2c). The degree of condensation of Q or T units, as determined by the ratios of the relative areas for different Q or T silicon connections (K. H. Wu, T. C. Chang, C. C. Yang, G. P. Wang, Thin Solid Films, 2006, 513, 84), improves with increased concentration of trialkoxysilane (3-MPTS or SiQAC) in the SqSHs (FIG. 2d). This is in agreement with the ATR-FTIR results (FIG. 2e), wherein cyclic Si—O—Si (~1080 cm$^{-1}$) (Q. Deng, B. Moore, K. A. Mauritz, Chem. Mater., 1995, 7, 2259) is apparent only in SqSH 1:1:1 and SqSH 1:2:1, both containing high organic components in the organosilica hybrids. Interestingly, while $T_3$ (fully-condensed trimeric species) dominates in the T units, all SqSHs as well as sol-gel silica present a large amount of $Q_3$ species bearing one hydroxyl group. This may be explained by the reasoning that hydrolyzed TEOS bearing four hydroxyl groups has more steric hindrance during condensation, compared with trialkoxysilanes with three hydroxyl groups. Thermogravimetric analysis (TGA) was performed to further characterize the synthesized SqSHs (FIG. 5a-c). The post-calcination residual inorganic mass increases with increasing feed ratios of TEOS to the trialkoxysilanes (3-MPTS and SiQAC), which is consistent with the $^{29}$Si NMR results.

Figure 3:
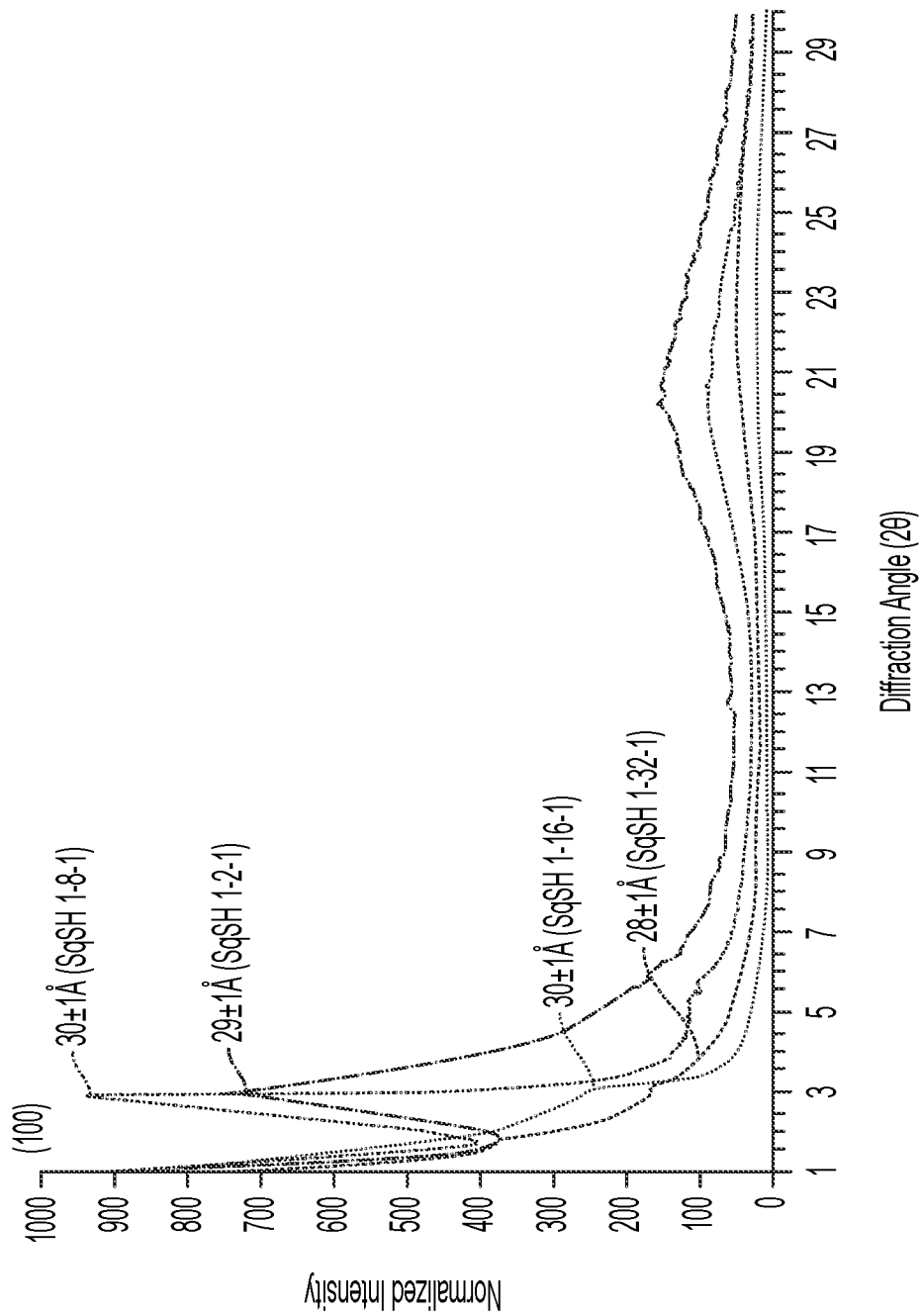
FIG. 3 shows small-angle powder X-ray diffraction (XRD) patterns of the SqSH 1:n:1 hybrids (n=2, 8, 16, 32)

By changing the feed ratios of TEOS to the trialkoxysilanes, ordered structures with variable d spacing within the spherical particles could be discerned by XRD and electron microscopy. The SiQAC molecule contains a long hydrophobic alkyl chain linked to the silicon atom by a Si—C bond, which is chemically stable under hydrolytic conditions. It becomes amphiphilic when silanol groups are formed during hydrolysis (A. Shimojima, K. Kuroda, Chem. Rec., 2006, 6, 53). Based on this amphiphilic assembly mechanism, lamellar mesostructures may be produced inside the hybrid silica particles within two hours using the Stöber route with a strong base (ammonium hydroxide) as catalyst. Small angle powder X-ray diffraction (XRD) patterns of the SqSH 1-n-1 hybrids (n=2, 8, 16, and 32) show diffraction peaks corresponding to the d spacing value of 2.9±0.1 nm (FIG. 3). One should note that these d values are smaller than that identified from condensed alkysiloxanes with bilayer lamellar structure (d=5.3 nm) A. Shimojima, Y. Sugahara, K. Kuroda, Bull. Chem. Soc. Jpn., 1997, 70, 2847), indicating a different molecular packing profile. Diffraction peak intensity becomes higher with the increased ratio of TEOS to SiQAC for SgSH 1-n-1 where n≤8. This implies that addition of increased concentrations of TEOS with strong three-dimensional network formation ability, leads to more highly-ordered siloxane networks with reduced mesoporosity. Incorporation of tetraalkoxysilane in the self-assembly process of alkyltrialkoxysilane also contributes to increasing the thermal stability, a feature that could not be attained by hydrolysis and condensation of alkyltrialkoxysilane alone (A. Shimojima, K. Kuroda, Langmuir, 2002, 18, 1144). The network-forming ability of TEOS was also verified by the observation that no particles were formed from hydrolytic co-condensation of the two trialkoxysilanes (SiQAC and 3-MPTS) in the absence of TEOS, under the present experimental conditions.

Figure 4A:
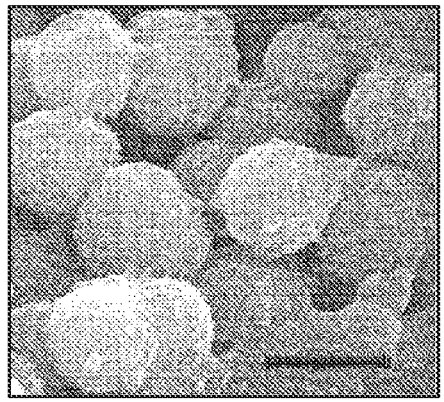
FIGS. 4a to f show electron micrographs.
Figure 4B:
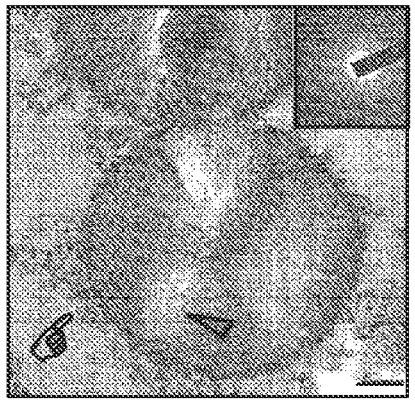
Figure 4C:
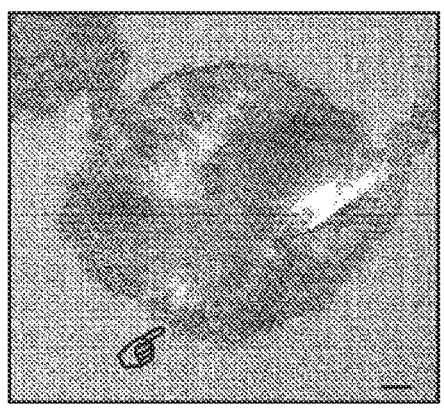
Figure 4D:
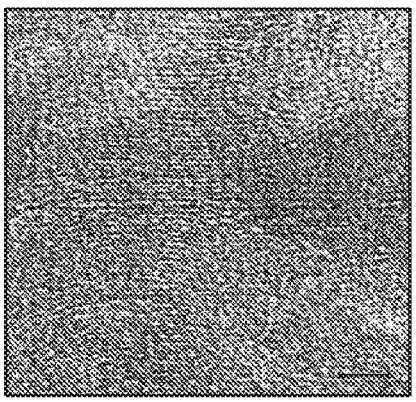
Figure 4E:
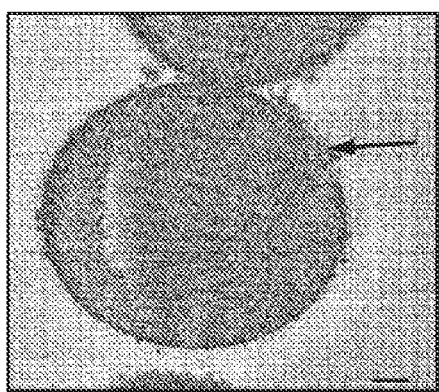
Figure 4F:
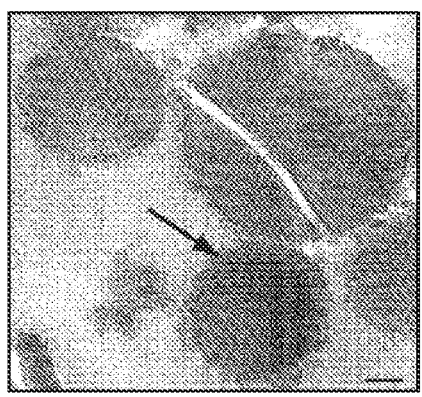
Figure 6:
FIG. 6 shows partial coalescence of SqSHs of one embodiment of the invention to form peanut-like structures. Unstained transmission electron microscopy image of the formation of partially coalesced, peanut-like particles derived from SqSH 1:4:1. This clumping phenomenon is observed in all SqSH versions with different feed ratios, but not for the sol-gel silica control. The process should have occurred while the SIQAC- and ethanol-stabilized droplets are in their liquid phase prior to solidification. It is possible that the quaternary ammonium trialkoxysilane (SiQAC) located on the surface of droplets with long hydrophobic alkyl chain protrudes from a lipophilic droplet into the continuous aqueous phase. Upon collision with another globule, these alkyl chains may pierce the other globule, making the droplets more prone to partial coalescence (E. Fredrick, P. Walstra, K. Dewettinck, Adv. Colloid Interface Sci. 2010, 153, 30). Scale bar=100 nm.
Figure 7B:
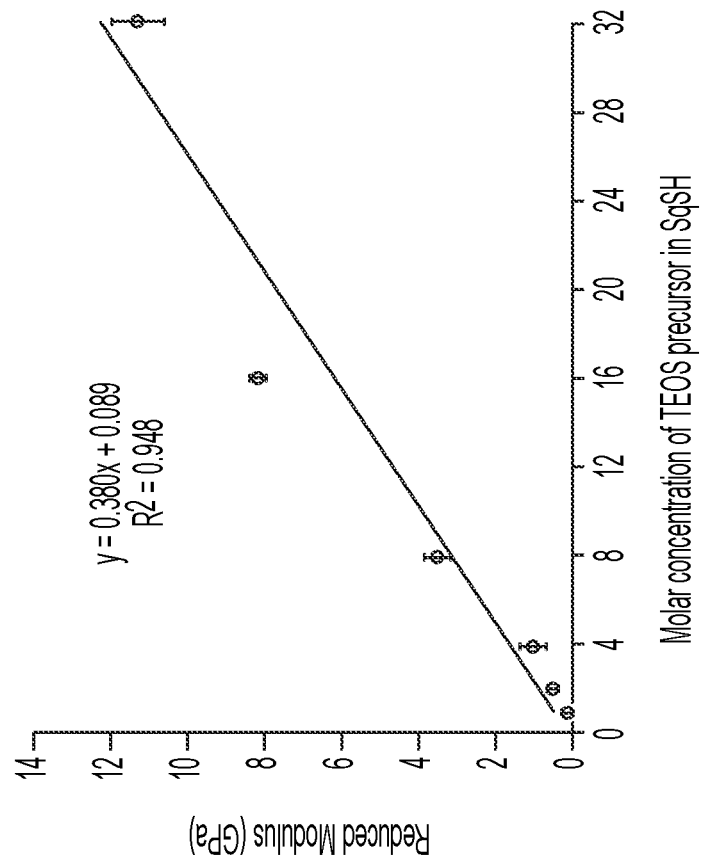
FIGS. 7a to 7d show mechanical testing (modulus and hardness).
Figure 7A:
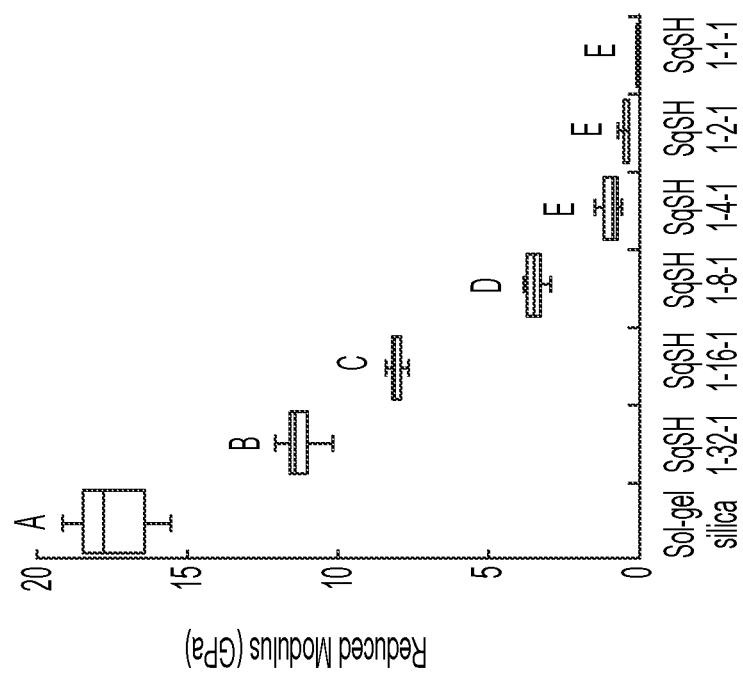
Figure 7D:
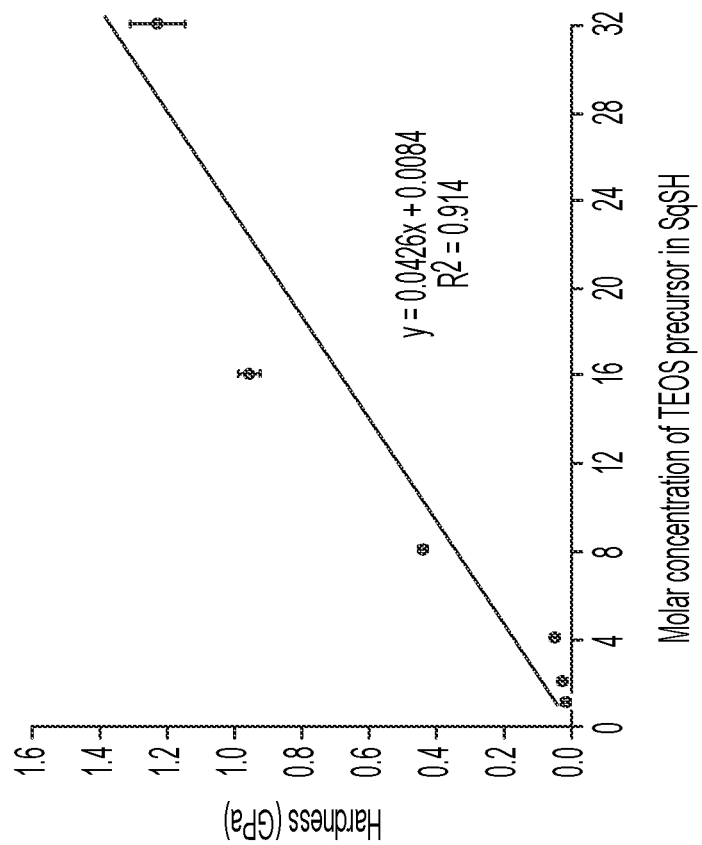
Figure 7C:
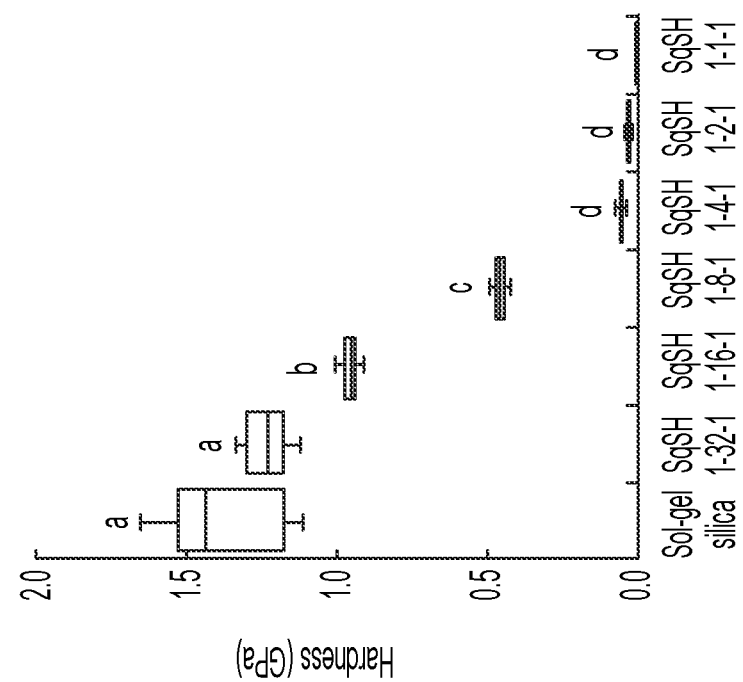

Sol-gel silica particles synthesized by the hydrolysis and condensation reactions of TEOS alone in the present study are monodisperse (~200 nm in diameter; data not shown), whereas the SqSH particles are slightly larger (ca. 250-1000 nm), and polydisperse, as revealed by scanning electron microscopy (SEM) (FIG. 4a). The SgSH particles exhibited a tendency to partially coalesce prior to solidification into particulates, producing peanut-like structures (FIG. 6). The morphology of these partially-coalesced SqSH particles is similar to the morphology of previously-reported particles prepared from the co-condensation of TEOS with aminopropyltriethoxysilane (APTES) via a Stöber-like route (S. Chen, S. Hayakawa, Y. Shirosaka, E. Fujii, K. Kawabata, K. Tsuru, A. Osaka, *J. Am. Ceram. Soc.*, 2009, 92, 2074). Unlike the TEOS-derived spherical silica particles which have smooth surfaces, the surfaces of the SqSH particles are rough, as observed using transmission electron microscopy (TEM), with small aggregates forming around the SqSH particle even after multiple ethanol rinses (FIG. 4b). These surface aggregates are possibly caused by self-condensation of SiQAC or 3-MPTS that are covalently bonded to the SqSH surface, as they were resistant to ethanol rinsing and sonication, and became sparser after calcination (FIG. 4c). For SqSH 1-n-1 (n 8), lamellar structures can be discerned by TEM at high magnification (FIG. 4d). For SqSH 1-n-1 (n>8) lamellar structures cannot be identified by TEM (F FIG. 4e); the SqSH particles became solid spheres after calcination (FIG. 4f).

Figure 9A:
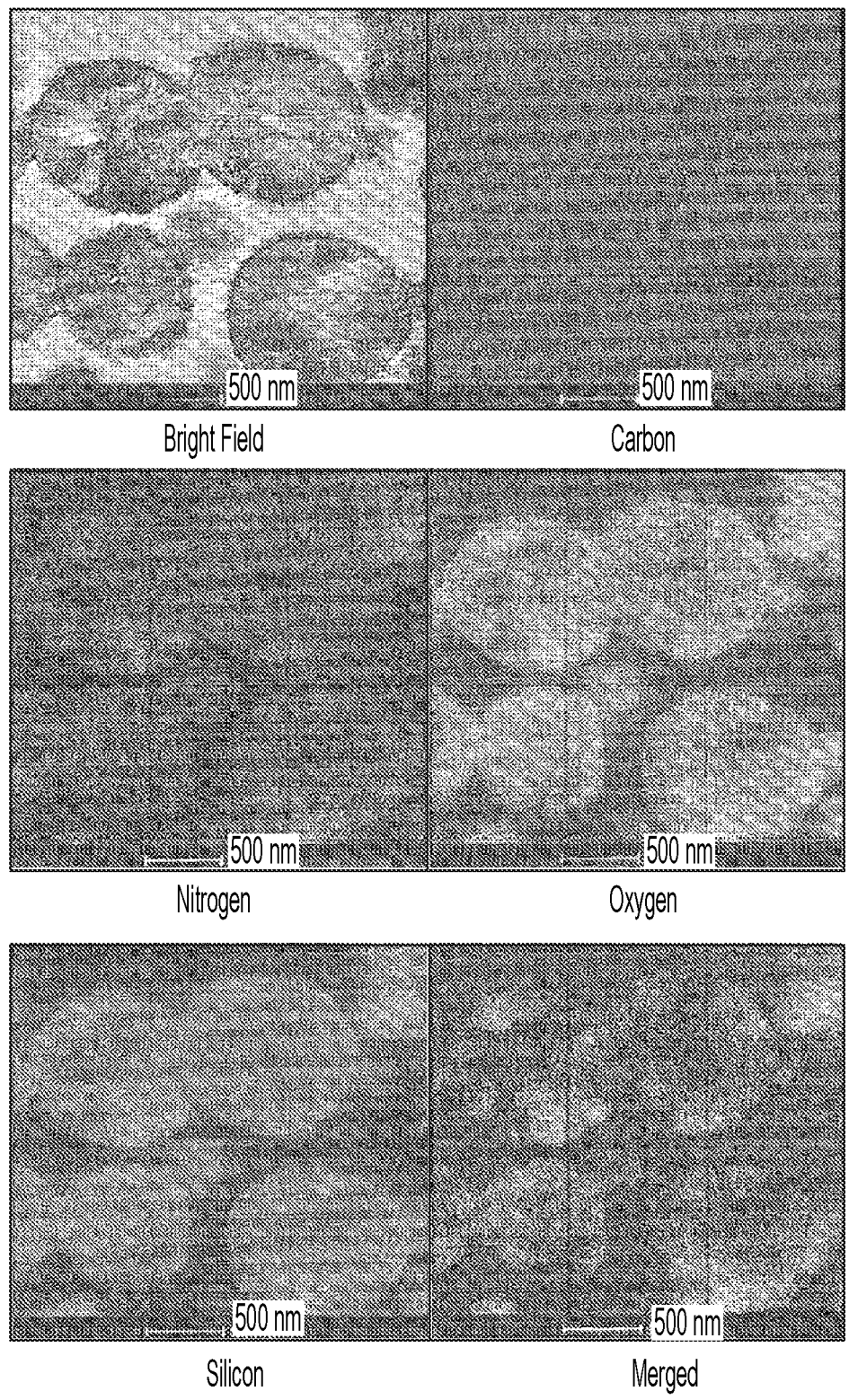
FIG. 9a shows scanning transmission electron microscopy energy dispersive X-ray analysis (STEM-EDX) mappings of distribution of carbon, nitrogen, oxygen, and silicon within SqSH (at molar ratio 1:8:1) of one embodiment of the invention.
Figure 9B:
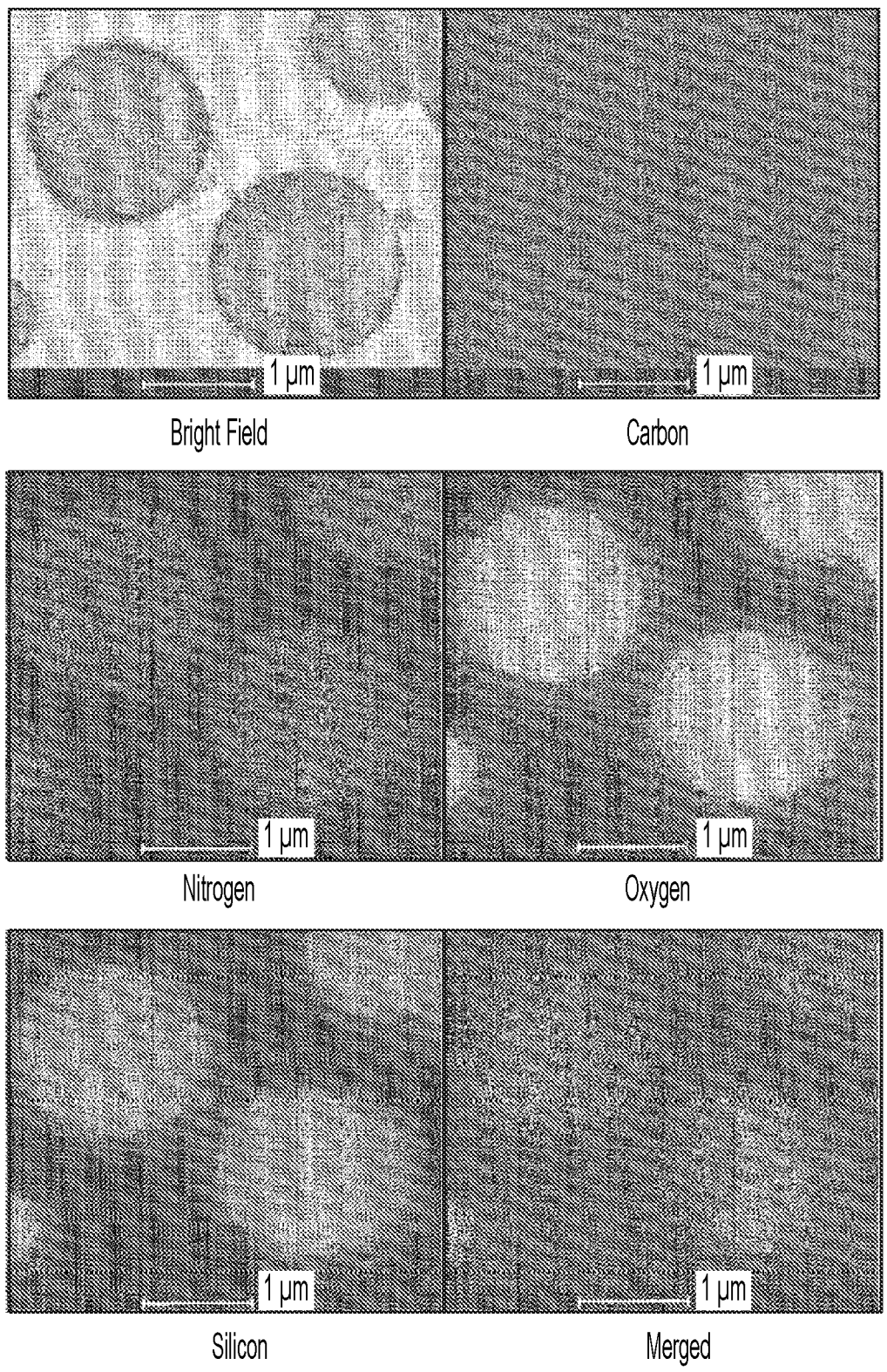
FIG. 9b shows scanning transmission electron microscopy-energy dispersive X-ray analysis (STEM-EDX) mappings of distribution of carbon, nitrogen, oxygen, and silicon within SqSH (at molar ratio 1:32:1) of another embodiment of the invention.

The presence of silicon, oxygen, nitrogen, carbon within SqSH 1:8:1 and SqSH 1:32:1 particles was confirmed using scanning transmission electron microscopy-energy dispersed X-ray analysis (STEM-EDX; FIG. 9a and FIG. 9b, respectively). Identification of nitrogen within the SqSH particles is indicative of the presence of the quaternary ammonium functionality (derived from SiQAC) within the entire particle. This is contrary to a grafting procedure in which the quaternary ammonium functionality is only present along the particle surface. The STEM-EDX data, however, does not permit conclusions to be drawn with respect to the methacryloxy functionality derived from 3-MPTS.

Mechanical Properties of SqSH Particles

Silsesquioxane-silica hybrids with different organic/inorganic compositions and variable structures should be modifiable in terms of mechanical and biological properties. The mechanical properties of SqSHs can be tuned by altering the TEOS molar feed ratio, so that particles with higher silica content can be produced. Nanoindentation performed on SqSH particles and sol-gel silica using the method reported by Oliver and Pharr (W. C. Oliver, G. M. Pharr, *J. Mater. Res.*, 1992, 7, 1564) revealed correlations between increases in reduced modulus and hardness, with increasing feed ratios of TEOS to the trialkoxysilane (FIGS. 7a-7d).

Antimicrobial Activities of SqSH Incorporated Bis-GMA/TEGDMA Resins

Figure 8A:
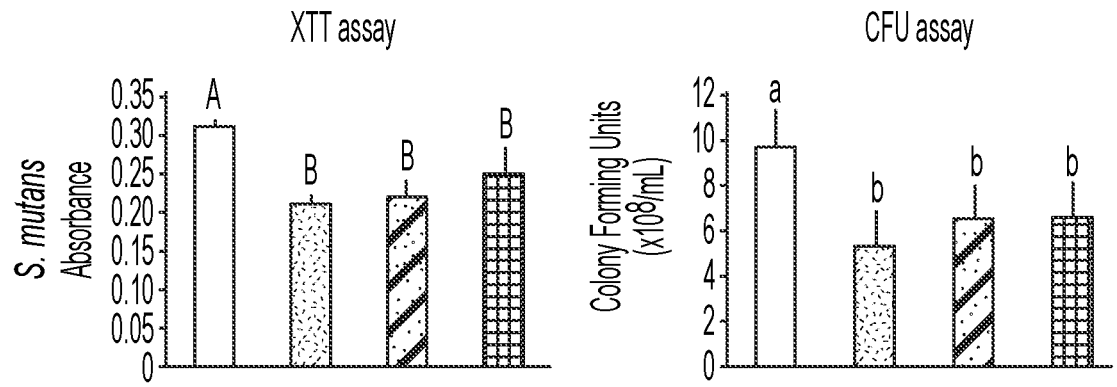
FIGS. 8a to 8c shows antimicrobial potentials with XTT and CFU assays against (a) S. mutans; (b) A. naeslundii; and (c) C. albicans.
Figure 8B:
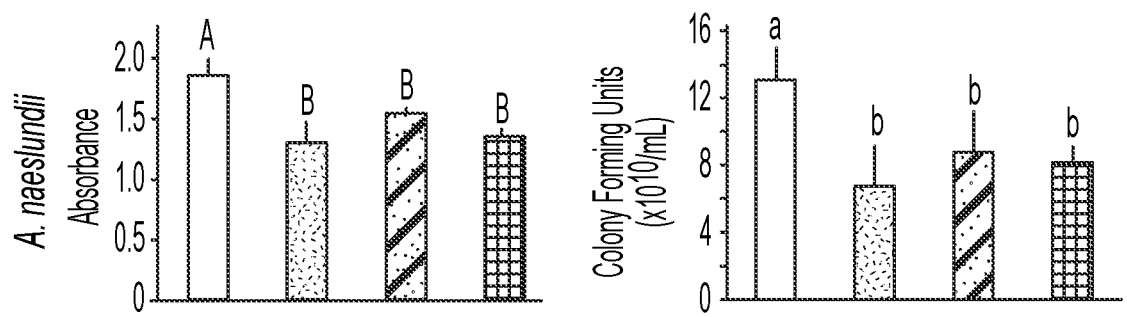
Figure 8C:
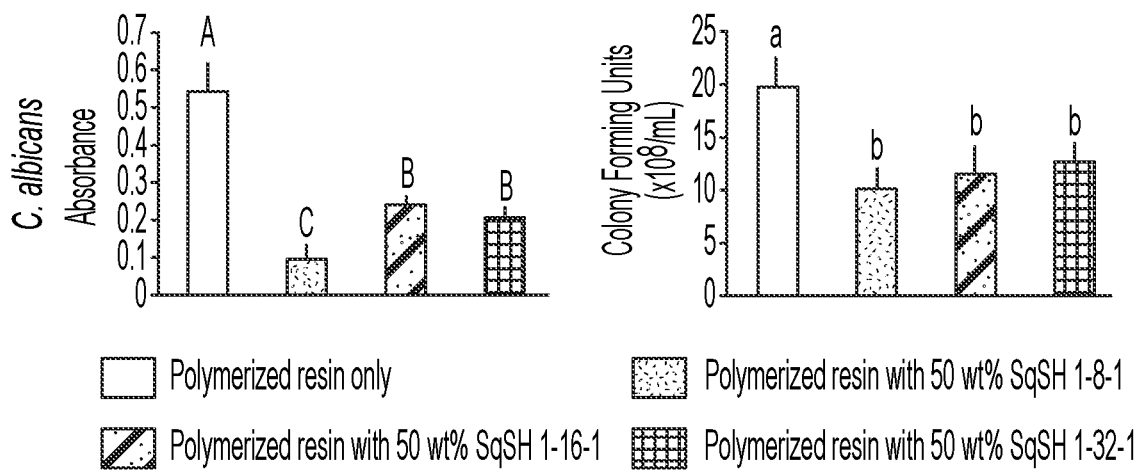

Because SqSHs bearing methacryloxy functional groups can be co-polymerized with methacrylate resin in the presence of certain catalysts (e.g. photoinitiator and tertiary amine accelerator), SqSHs with different TEOS-trialkoxysilanes molar feed ratios are added into a resin blend consisting of 2,2-bis[4-(2-hydroxy-3-methacryloxypropoxy)phenyl]propane (bis-GMA) and triethylene glycol dimethacrylate (TEGDMA), with camphorquinone (CO) and ethyl(4-dimethylamino)benzoate (EDMAB) as the photoinitiator and accelerator, respectively. Incorporation of the SqSH organic-inorganic hybrid particles into the methacrylate resin blend results in a series of antimicrobial resin composites that may be used for restoring teeth and preventing recurrent decay caused by colonization of bacterial biofilms around the margins of the tooth fillings. Three SqSH-containing resin composites (SqSH 1:8:1, 1:16:1 and 1:32:1) were chosen in the present study due to their relatively high reduced modulus and hardness, when compared to sol-gel silica, which are desirable properties for preparing restorative resin composites. Previous studies have demonstrated that incorporation of SiQAC-derived sol-gel reaction products confers resinous materials with antimicrobial activities against bacteria and fungi (S.-q.Gong, L.-n. Niu, Kemp L. K., C. K. Y. Yiu, H. Ryou, Y.-p. Qi, J. D. Blizzard, S. Nikonov, M. G. Brakkett, R. L. W. Messer, C. D. Wu, J. Mao, L. B. Brister, F. A. Rueggeberg, D. D. Arola, D. H. Pashley, F. R. Tay, *Acta Biomater.*, 2012, 8, 3270; S. Q. Gong, J. Epasinghe, F. A. Rueggeberg, L. N. Niu, D. Mettenberg, C. K. Y. Yiu, J. D. Blizzard, C. D. Wu, J. Mao, C. L. Drisko, D. H. Pashley, F. R. Tay, *PLoS One*, 2012, 7, e42355; S. Q. Gong, D. J. Epasinghe, B. Zhou, L. N. Niu, K. A. Kimmerling, F. A. Rueggeberg, C. K. Y. Yiu, J. Mao, D. H. Pashley, F. R. Tay, *Acta Biomater.*, 2013, 9, 6964). The antimicrobial potentials of SqSH-containing methacrylate resins against *Streptococcus mutans*, *Actinomyces naeslundii*, and *Candida albicans* were confirmed using 2,3-bis-(2-methoxy-4-nitro-5-sulfophenyl)-2H-tetrazolium-5-carboxanilide (XTT) and Colony Forming Unit (CFU) assays (FIGS. 8a-c). *Streptococcus mutans* and *A. naeslundii* are cariogenic oral pathogens, while *C. albicans* is associated with oral candidiasis in susceptible hosts. It is likely that the antimicrobial activities of SqSH containing methacrylate resins are permanent and non-leaching (S. Q. Gong, J. Epasinghe, F. A. Rueggeberg, L. N. Niu, D. Mettenberg, C. K. Y. Yiu, J. D. Blizzard, C. D. Wu, J. Mao, C. L. Drisko, D. H. Pashley, F. R. Tay, *PLoS One*, 2012, 7, e42355; S. Q. Gong, D. J. Epasinghe, B. Zhou, L. N. Niu, K. A. Kimmerling, F. A. Rueggeberg, C. K. Y. Yiu, J. Mao, D. H. Pashley, F. R. Tay, *Acta Biomater.*, 2013, 9, 6964), as SqSH particles are co-polymerized with the methacrylate network. This non-leaching antimicrobial activity is independent of the loss of surface layer of the composite by wear during function, since SqSH particle are dispersed throughout the bulk resin matrix.

Figure 10A:
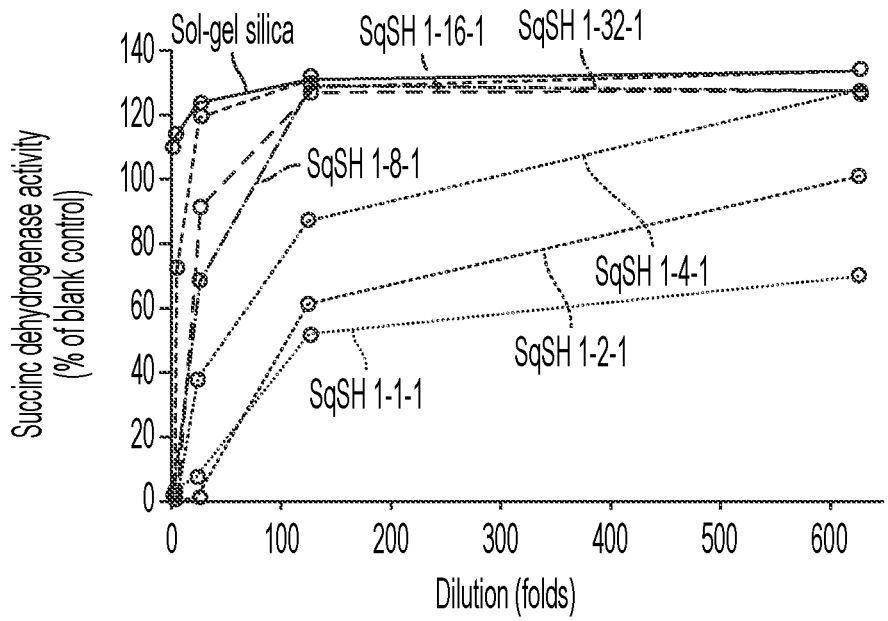
FIGS. 10A and 10B show cytotoxicity of one embodiment of the invention and a comparative sol-gel silica.
Figure 10B:
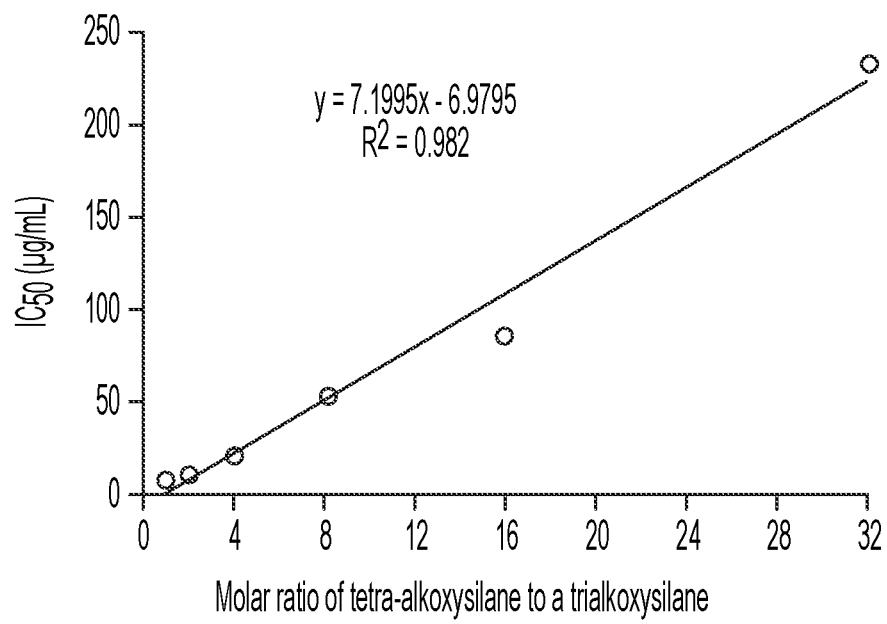

Because materials that possess antimicrobial properties against bacteria or fungi may be toxic to mammalian cells, we performed 3-(4,5-dimethylthiazol-2-yl)-2,5-diphenyltetrazolium bromide (MTT) assay on a mouse fibroblast cell line (L929) to examine the effects of increasing molar feed ratios of SIQAC on the cytotoxicity of SqSHs (FIGS. 10a-b). The results demonstrate a significant positive correlation between the 50% reduction in cell viability ($IC_{50}$) of the mammalian cells and the molar feed ratio of TEOS employed for the synthesis of the SqSH particles.

Mesoporous antimicrobial SqSH particles with spherical morphology and lamellar structures may also be used as absorbents or carriers for loading bioactive agents, such as growth factors, catalysts, metal ions, and photoactive molecules, to achieve other functions. Other alkoxysilanes with different organofunctional moieties (e.g., acrylate, methacrylate, ($C_2$-$C_8$)alkenyl, glycidyloxy, epoxy, sulfonate, carboxylate, ester, amino, acrylamide, methacrylamide, isocyanato, amino acid, nucleic acid, mercapto($C_1$-$C_6$)alkyl, and the like) may be used in lieu of 3-MPTS, enabling these hybrid particles to satisfy different product requirements. The versatile functionality of these hybrid materials will expand the range of their applications in various fields. For example, antimicrobial SqSH particles containing acrylate functionalities may be incorporated into acrylate-based paints; antimicrobial SqSH particles containing vinyl functionalities may be blended with polypropylene via an extruder to produce antimicrobial food wraps for the food industry.

CONCLUSIONS

A facile method has been developed for synthesizing unique SqSH hybrid silica particles via a Stöber-like approach, with ordered lamellar structures with spherical morphology, without the use of additional surfactants. The one-pot synthesis approach leads to the development of unique and useful antimicrobial hybrid silica particles with quaternary ammonium groups distributed within the entire particles, and therefore, non-leaching antimicrobial activities, as opposed to a grafting procedure, where thus type of functionality is present only along the particle surface. Moreover, antimicrobial activities are present irrespective of the degree of mesoscopic order of the hybrid silica particles. This synthesis approach may be further expanded by replacing the curing functionality with other organofunctional moieties, thereby enabling the antimicrobial hybrid particles with tunable mechanical properties to be incorporated into different polymers/copolymers for a wide range of commercial applications. Likewise, this synthesis approach may be further expanded by replacing the antimicrobial functionality with other organofunctional moieties, thereby enabling the antimicrobial hybrid particles with tunable biological properties to be incorporated into different polymers/copolymers for a wide range of commercial applications.

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A tooth desensitizer, comprising a solution comprising at least one filling material selected from the group consisting of siloxanes, glass ionomers, methacrylates, and silver amalgams; and a silsesquioxane-silica hybrid, wherein the silsesquioxane-silica hybrid comprises:
   a silica particle covalently bound to:
   (1) a residue having the formula:
   wherein:

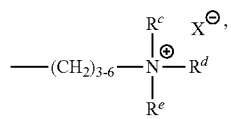

$R^c$ is $(C_{1-2})$alkyl;
$R^d$ is $(C_{1-2})$alkyl or phenyl;
$R^e$ is $(C_{6-22})$alkyl;
$X^-$ is an anion selected from the group consisting of chloride, bromide, fluoride, iodide, sulfonate, and acetate; and
(2) a residue comprising a curing group selected from the group consisting of acrylate, methacrylate, $(C_2-C_8)$ alkenyl, glycidyloxy, epoxy, sulfonate, carboxylate, ester, amino, acrylamide, methacrylamide, isocyanato, amino acid, nucleic acid, mercapto$(C_1-C_6)$alkyl, and combinations thereof,
   wherein the solution is a water solution or a water-alcohol solution.

2. The tooth desensitizer of claim 1, wherein the curing group selected from the group consisting of acrylate, methacrylate, $(C_2-C_8)$alkenyl, acrylamide, methacrylamide, and combinations thereof.

3. The tooth desensitizer of claim 1, the curing group is methacrylate.

4. The tooth desensitizer of claim 1, the curing group is methacryloxypropyl.

5. The tooth desensitizer of claim 1, wherein $R^c$ is methyl.

6. The tooth desensitizer of claim 1, wherein $R^d$ is methyl.

7. The tooth desensitizer of claim 1, wherein $R^e$ is octadecyl.

8. The tooth desensitizer according to claim 1, further comprising at least one co-monomer is selected from the group consisting of $(C_2-C_8)$ alkene, vinyl chloride, acrylate, methacrylate, acrylamide, methacrylamide, and combinations thereof.

9. A kit, comprising:
   (a) a plurality of silsesquioxane-silica hybrid particles, wherein the silsesquioxane-silica hybrid particles comprises:
   silica covalently bound to:
   (1) a residue having the formula:

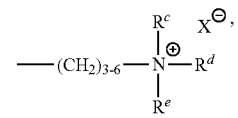

wherein:
$R^c$ is $(C_{1-2})$alkyl;
$R^d$ is $(C_{1-2})$alkyl or phenyl;
$R^e$ is $(C_{6-22})$alkyl;
$X^-$ is an anion selected from the group consisting of chloride, bromide, fluoride, iodide, sulfonate, and acetate; and
(2) a residue comprising a curing group selected from the group consisting of acrylate, methacrylate, $(C_2-C_8)$ alkenyl, glycidyloxy, epoxy, sulfonate, carboxylate, ester, amino, acrylamide, methacrylamide, isocyanato, amino acid, nucleic acid, mercapto$(C_1-C_6)$alkyl, and combinations thereof; and
(b) at least one polymerization initiator,
   wherein the kit further comprises a natural rubber, a synthetic rubber, a thermoplastic polymer, or a combination thereof.

10. The kit according to claim 9, further comprising at least one synergist, at least one filler, or at least one co-monomer.

11. The kit according to claim 10, further comprising at least one co-monomer selected from the group consisting of $(C_2-C_8)$ alkene, vinyl chloride, acrylate, methacrylate, acrylamide, methacrylamide, and combinations thereof.

12. The kit according to claim 11, wherein said co-monomer is selected from the group consisting of methyl methacrylate, ethylene, propylene, hydroxyethyl methacrylate, 1, 6-hexanediol dimethacrylate, bisphenol A-glycidyl methacrylate (bis-GMA), triethylene glycol dimethacrylate (TEGMA), urethane dimethacrylate, and combinations thereof.

13. The kit according to claim 9, wherein said plurality of particles has an average particle size of about 50 nm to about 2000 nm.

14. The kit according to claim 9, wherein said plurality of particles has a polydispersity index (PDI=$M_w/M_n$) of about 1 to about 20.

15. The kit according to claim 9, wherein the kit further comprises a natural rubber, a synthetic rubber, or a combination thereof.

16. The kit according to claim 9, wherein the kit further comprises a thermoplastic polymer.

* * * * *